US006998263B2

(12) United States Patent
Kovesdi et al.

(10) Patent No.: US 6,998,263 B2
(45) Date of Patent: Feb. 14, 2006

(54) METHODS OF PREPARING AND USING A VIRAL VECTOR LIBRARY

(75) Inventors: Imre Kovesdi, Rockville, MD (US); Duncan L. McVey, Derwood, MD (US); Thomas J. Wickham, Germantown, MD (US); Joseph T. Bruder, Ijamsville, MD (US); Douglas E. Brough, Olney, MD (US)

(73) Assignee: GenVec, Inc., Gaithersburg, MD (US)

( * ) Notice: Subject to any disclaimer, the term of this patent is extended or adjusted under 35 U.S.C. 154(b) by 621 days.

(21) Appl. No.: 09/780,526

(22) Filed: Feb. 9, 2001

(65) Prior Publication Data

US 2001/0026794 A1    Oct. 4, 2001

Related U.S. Application Data

(60) Provisional application No. 60/181,321, filed on Feb. 9, 2000, provisional application No. 60/205,269, filed on May 18, 2000, provisional application No. 60/209,158, filed on Jun. 2, 2000.

(51) Int. Cl.
*C12N 15/63* (2006.01)
*C12N 7/01* (2006.01)

(52) U.S. Cl. .............................. 435/320.1; 435/235.1; 435/DIG. 22; 435/DIG. 23; 536/23.1; 536/24.1

(58) Field of Classification Search .............. 435/239, 435/320.1, 325, 366, 367, 368, DIG. 22, 435/DIG. 23, DIG. 24, 235.1; 536/23.1, 536/24.1
See application file for complete search history.

(56) References Cited

U.S. PATENT DOCUMENTS

| 5,270,170 | A |   | 12/1993 | Schatz et al. |   |
|---|---|---|---|---|---|
| 5,593,972 | A |   | 1/1997 | Weiner et al. |   |
| 5,622,699 | A |   | 4/1997 | Ruoslahti et al. |   |
| 5,703,057 | A |   | 12/1997 | Johnston et al. |   |
| 5,733,731 | A | * | 3/1998 | Schatz et al. | 435/6 |
| 5,783,386 | A |   | 7/1998 | Jacobs, Jr. et al. |   |
| 5,817,637 | A |   | 10/1998 | Weiner et al. |   |
| 5,830,876 | A |   | 11/1998 | Weiner et al. |   |
| 5,939,250 | A |   | 8/1999 | Short |   |
| 5,955,275 | A |   | 9/1999 | Kamb |   |
| 5,958,672 | A |   | 9/1999 | Short |   |
| 5,981,505 | A |   | 11/1999 | Weiner et al. |   |
| 5,989,553 | A |   | 11/1999 | Johnston et al. |   |
| 6,001,557 | A | * | 12/1999 | Wilson et al. | 435/5 |
| 6,156,511 | A | * | 12/2000 | Schatz et al. | 435/6 |
| 6,440,728 | B1 | * | 8/2002 | McVey et al. | 435/320.1 |
| 6,447,768 | B1 | * | 9/2002 | van Zonneveld et al. | 424/93.2 |

FOREIGN PATENT DOCUMENTS

| WO | WO 94/16737 A | 8/1994 |
|---|---|---|
| WO | WO 95/17511 A | 6/1995 |
| WO | WO 96/25506 A | 8/1996 |
| WO | WO 96/31613 A | 10/1996 |
| WO | WO 97/20918 A | 6/1997 |
| WO | WO 98/13485 A | 4/1998 |
| WO | WO 98/13487 A | 4/1998 |
| WO | WO 98/32860 A | 7/1998 |
| WO | WO 98/36097 A | 8/1998 |
| WO | WO 98/39483 A | 9/1998 |
| WO | WO 98/56937 A | 12/1998 |
| WO | WO 99/15686 A | 4/1999 |
| WO | WO 99/36516 A | 7/1999 |
| WO | WO 99/41368 A | 8/1999 |
| WO | WO 99/41369 A | 8/1999 |
| WO | WO 99/41383 A | 8/1999 |
| WO | WO 99/41402 A | 8/1999 |
| WO | WO 99/43843 A | 9/1999 |
| WO | WO 99/45151 A | 9/1999 |
| WO | WO 99/64582 A | 12/1999 |
| WO | WO 00/05406 A | 2/2000 |
| WO | WO 01/25463 A | 4/2001 |

OTHER PUBLICATIONS

Webster's II New Riverside University Dictionary, 1994, Houghton Mifflin Comapny, pp. 690 and 281.*
Bett et al., *PNAS USA, 91* (1), 8802-8806 (Sep. 1994).
Fu et al., *Hum. Gene Ther.*, 8 (11), 1321-1330 (Jul. 20, 1997).
Hardy et al., *J. Virol.*, 71 (3), 1842-1849 (Mar. 1997).

(Continued)

*Primary Examiner*—Andrew Wang
*Assistant Examiner*—My-Chau T. Tran
(74) *Attorney, Agent, or Firm*—Leydig, Voit & Mayer, Ltd.

(57) ABSTRACT

The present invention provides a library of viral vectors, wherein each member comprises a first heterologous DNA encoding a first gene product and a second heterologous DNA encoding a second gene product. The first heterologous DNA is common to each member of the library, while the second heterologous DNA varies between members of the library. The present invention additionally provides a method of constructing a library of viral vectors. The method comprises carrying out homologous recombination between a first DNA molecule and a second DNA molecule to form a pool of intermediate viral vector genomes. One or more linear third DNA molecules are ligated into the pool of intermediate viral genomes to produce a library of viral vector genomes. Alternatively, homologous recombination between linear DNA molecules and recipient DNA molecules produces a library of viral vector genomes. The library of viral vector genomes is converted into a library of viral vectors.

6 Claims, 1 Drawing Sheet

OTHER PUBLICATIONS

Murphy et al., *PNAS USA*, 84 (23), 8277-8281 (Dec. 1987).
Tashiro et al., *Hum. Gene Ther.*, 10 (11), 1845-1852 (Jul. 20, 1999).
Chartier et al., *J. Virol.*, 70 (7), 4805-4810 (1996).
He et al., *PNAS USA*, 95 (5), 2509-2514 (Mar. 3, 1998).
Imler et al., *Gene Ther.*, 2 (4), 263-268 (Jun. 1, 1995).

* cited by examiner

METHODS OF PREPARING AND USING A VIRAL VECTOR LIBRARY

CROSS REFERENCE TO RELATED PATENT APPLICATIONS

This application claims priority to U.S. Provisional Patent Application No. 60/181,321, filed Feb. 9, 2000, and U.S. Provisional Patent Application No. 60/205,269, filed May 18, 2000, and U.S. Provisional Patent Application No. 60/209,158, filed Jun. 2, 2000.

FIELD OF THE INVENTION

The present invention relates to an adenoviral vector library and methods of preparing and using same.

BACKGROUND OF THE INVENTION

The DNA and protein sciences have made great strides over the past two decades. Researchers have accomplished the previously unthinkable by sequencing the entire genomes of several microorganisms. The genomes of several higher eukaryotes, including mammals, are nearly completely sequenced and available on a variety of databases. Although sequenced, much of the genome remains a mystery as to the function of the gene products. An important area of genetic research is matching nucleotide sequences with a cellular function or activity.

Similarly, researchers have developed technology to enable rapid determination of the amino acid sequence of a selected protein or peptide. Peptide sequencing reactions that previously took days to accomplish can now be completed in mere hours, the results of which are presented in a meaningful format. Large amounts of information regarding nucleic acid sequences and amino acid sequences have been entered into databases around the world. This rapid dissemination of information has enabled those in the art to associate a function with proteins that have similar functions in different species of organisms. It is further possible to associate a function to short amino acid motifs of these proteins. Functional motifs, or nucleic acid sequences or amino acid sequences commonly associated with a particular function, can aid in predicting the function or activity of a peptide. For example, many proteins associated with carbohydrate metabolism may comprise a similar active site. An unknown protein that also comprises the amino acid sequence of the identified active site might be predicted to be involved in carbohydrate metabolism. However, proposed functional motifs can vary in activity depending on surrounding sequences, location of the peptide in a cell, and the type of host cell, thereby complicating any assumptions regarding peptide function.

Potential use of the sequence information collected to date is limitless if links between genetic sequence and cell function can be established. Therapeutic peptides, disease indicators, regulatory mechanisms, and the like are waiting to be discovered in the sequence code. In addition, the compiled sequence information may also provide insight into the functional relationships between gene products. Such information will be sought after as biotechnology companies search for combinations of biological factors to be used as treatment modalities in the next generation of gene therapy products.

In order to capitalize on the seemingly endless supply of sequenced genomes, researchers have developed genetic libraries that can be screened to associate a nucleic acid sequence with a protein or peptide or cellular function. In many instances, detection involves hybridizing to the unknown DNA sequence a probe specific for a desired sequence. Yet, as discussed above, peptide function cannot be accurately predicted by the mere presence of motifs. Alternatively, nucleic acid sequences are incorporated into a vector and introduced into a host cell. The gene product encoded by the nucleic acid is expressed and detected. Often, screening is accomplished in vitro (see, for example, DeGraaf et al., *Gene*, 128 (1), 13–17 (1993)). Some methods of screening proteins or peptides involve the formation of fusion proteins. However, incorporating, for example, a marker peptide with an unknown peptide of interest may interfere with the normal functioning of both peptides.

Other methods of using libraries require a physical association between the peptide of interest and the nucleic acid that encodes the peptide. For example, U.S. Pat. No. 5,270,170 (Schatz et al.) describes a method of generating and screening random peptides comprising putative ligands that bind to target receptor molecules. A random peptide library is prepared such that the random peptide is expressed as a fusion protein comprising the random peptide and a DNA binding protein. The DNA binding protein will bind to the recombinant DNA expression vector that encodes the fusion product containing the peptide of interest. Therefore, once a peptide is identified, the corresponding expression vector is readily available. However, the nucleic acid molecule that encodes the fusion product must comprise a binding site for the DNA binding protein. Furthermore, fusion of a random peptide with a DNA binding protein can interfere with the functioning of the random peptide by altering or blocking active sites, disrupting protein folding, and the like. Phage peptide display libraries are also used to express and screen proteins for binding to a target molecule. Phage display libraries have been used to screen proteins in vitro by association of the expressed peptide with a target ligand. However, the utility of phage display libraries to associate function with a genetic sequence in vitro is limited in that few target molecules have been identified, much less successfully expressed in their native conformation. Phage display libraries also have been utilized to identify peptides in vivo (see, for example, U.S. Pat. No. 5,622,699 (Ruoslahti et al.)). Yet, gene products identified by function in the context of phage may not necessarily have similar function or activity in other contexts or environments. For example, phage have limited utility in screening in vitro and in vivo for ligands that are efficiently internalized within a cell.

Aside from the technical difficulties associated with screening library-encoded gene products, construction of genetic libraries as described in the prior art is time and labor intensive. For example, methods that require formation of fusion proteins necessitate an understanding of the nucleic acid sequence encoding the random peptide. Extensive manipulation of the nucleic acid sequence is also required. Moreover, the level of transduction efficiency for vectors commonly used to generate genetic libraries, such as plasmids, is low, further complicating the expression and screening of encoded gene products. Vectors with greater transduction efficiency are routinely constructed via homologous recombination. Yet, homologous recombination is time consuming and difficult to perform in large scale. If a skilled artisan attempts to construct expression vectors using homologous recombination and does not create the desired vector, the artisan will not be able to readily distinguish between the need to modify the construction technique and the possibility that the vector is not viable or does not encode the selected function. When working with a multiplicity of genetic elements encoding unknown products, this dilemma is even more complicated. Current vector construction techniques lack the flexibility and means of selection required to efficiently produce expression vectors used to generate a genetic library.

In view of the above, there is a need in the art for an efficient and reliable method for using a genetic library to associate functions to nucleic acid sequences. In particular, there remains a need for a method of identifying functionally-related coding sequences. There also remains a need in the art for a reliable method for constructing a genetic library. The present invention seeks to satisfy at least some of these needs. The present invention is directed to multi-gene genetic libraries and methods of identifying functionally-related coding sequences. The present invention is further directed to a method of constructing a genetic library comprising or consisting of a multiplicity of vectors. These and other advantages of the present invention, as well as additional inventive features, will be apparent from the description of the invention provided herein.

BRIEF SUMMARY OF THE INVENTION

The present invention is directed to a library of viral vectors, wherein each member of the library comprises a first heterologous DNA and a second heterologous DNA. The first heterologous DNA is common to each member of the library of viral vectors and encodes a first gene product. The second heterologous DNA varies between the members of the library of viral vectors and encodes a second gene product. Preferably, the library of viral vectors is a library of adenoviral vectors.

The present invention also provides a method of constructing a library of viral vectors. The method comprises carrying out homologous recombination between a first DNA molecule and a second DNA molecule to produce a homologously recombined pool of intermediate viral genomes. The second DNA molecule is a recipient DNA molecule comprising all or part of a viral genome. The method further comprises ligating one or more linear third DNA molecules into the pool of intermediate viral genomes to produce a library of viral vector genomes, wherein one or more linear third DNA molecules encode a potentially desirable feature. In another embodiment, the library of viral vector genomes is constructed by carrying out homologous recombination between linear DNA molecules and recipient DNA molecules, which comprise a dual selection cassette (DSC). No matter the embodiment, the library of viral vector genomes is transduced into a first population of host cells to convert the library of viral vector genomes into a library of viral vectors.

Preferably, the library of viral vector genomes, e.g., adenoviral vector genomes, comprises a multiplicity of genetic elements and is assembled simultaneously in a single reaction. The present inventive method can further comprise transducing a second population of host cells with the library of adenoviral vectors to select a viral vector comprising a desirable feature. The recipient DNA molecules desirably comprise at least one nucleic acid sequence encoding a gene product other than that encoded by the linear DNA fragments, wherein the nucleic acid sequence is common to each member of the library of viral vectors. The materials and methods described herein allow for the generation and use of eukaryotic expression libraries in the study of functional genomics and the like.

DETAILED DESCRIPTION OF THE INVENTION

Figure 1:
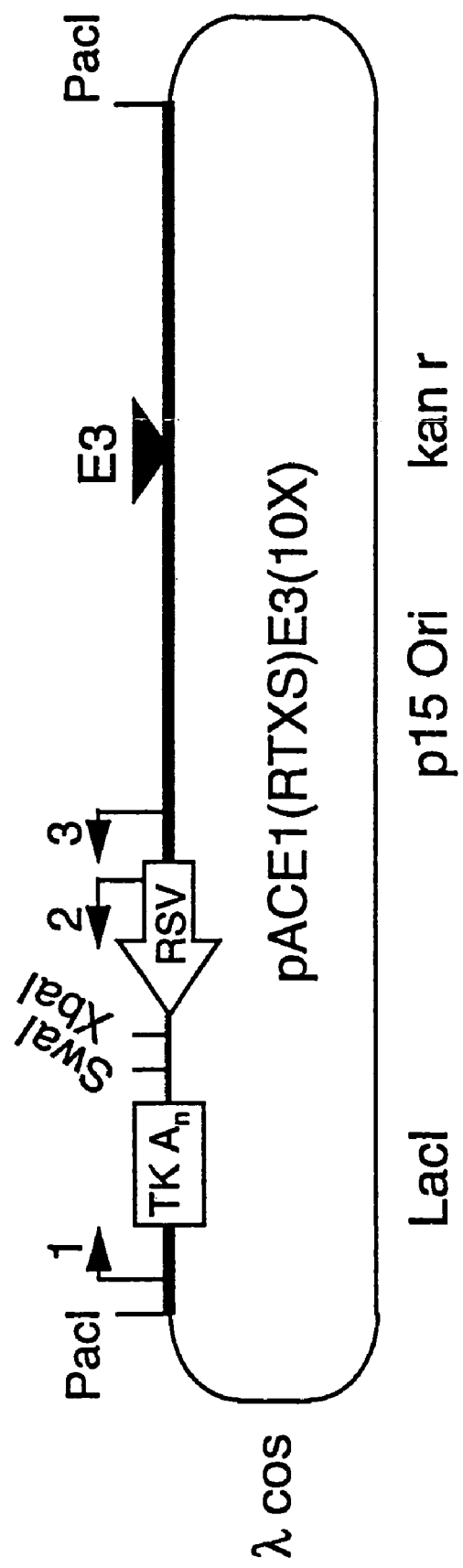
FIG. 1 depicts an exemplary recipient DNA molecule, pACE1(RTXS)E3(10X), described in Example 1.

The present invention is predicated, at least in part, on the discovery that viral vectors, in particular adenoviral vectors, can be constructed to comprise an assortment of genetic elements and, in turn, can be used to efficiently screen the function of the proteins, peptides, or functional nucleic acid sequences encoded by the assortment of genetic elements in vitro and in vivo. As such, the present invention is directed to a genetic library useful for elucidating the function of coding sequences. In particular, the genetic library of the present invention can be used to identify functionally-related coding sequences or coding sequences that act in concert to produce a biological effect. The present invention further provides a method of constructing a viral library comprising or consisting of a multiplicity of viral vectors comprising a multiplicity of genetic elements, as well as methods of using a library of viral vectors.

As the genetic code is unraveled, researchers will increasingly require tools to study the functional characteristics of biologically active gene products. Currently available assays for screening gene products provide only a glimpse of the role of a gene product in vivo and can be used only to broadly categorize biological factors. However, a biological factor often works in concert with other biologically-active molecules to affect a cellular response. Indeed, to fully characterize a gene product it is useful to examine the function of a biologically-active factor in the presence of known gene products. For example, previously described genomic libraries have been utilized to identify key genes involved in specific diseases or biological functions. However, once a gene is identified with a central role in a function or disease, it is not obvious how functionally related genes or genes in the same cellular pathway can be identified. Identifying peptides and, optionally, their coding sequences, that might be structurally and even functionally unrelated, but could synergize or repress each other in the context of a multi-factorial biological function or disease is not trivial.

Therefore, the present invention provides a library of viral vectors, such as adenoviral vectors, wherein each member of the library comprises a first heterologous DNA encoding a first gene product and a second heterologous DNA encoding a second gene product. The first heterologous DNA is common to each member of the library of viral vectors, while the second heterologous DNA varies between the members of the library of viral vectors. In other words, a gene or a set of genes is kept constant in all individual members of the viral library. To find, for example, new functions related to the peptide(s) encoded by each member of the library, a second heterologous DNA, which is varied throughout the library, is expressed from the same vector. One of ordinary skill in the art will appreciate that more than one "second" DNA can be inserted into each member of the library of viral vectors. One of ordinary skill in the art also will appreciate that the "first" DNA and the "second" DNA can each encode multiple gene products, depending on the particular embodiment of the present invention. In the present inventive library, at least one DNA is held constant in each member of the library, while at least one DNA varied throughout the members of the library. The present invention allows for the identification of related gene functions centered around a known function, that of the first DNA-encoded gene product.

Any viral vector that infects host cells and is capable of expressing nucleic acid sequences is appropriate for the present inventive library. Suitable viral vectors include, but are not limited to, adeno-associated virus (AAV)-based vectors, retroviral vectors, herpes simplex virus (HSV)-based vectors, AAV-adenoviral chimeric vectors, and adenovirus-based vectors. Adenovirus-based vectors are particularly suited for use in multi-gene virus libraries due to the large insert capacity available. An "adenovirus" is any virus of the family Adenoviridae, and desirably is of the genus *Mastadenovirus* (e.g., mammalian adenoviruses) or *Aviadenovirus* (e.g., avian adenoviruses). Adenoviral stocks that can be employed as a source of adenoviral genomes can be amplified from the adenoviral serotypes 1 through 51, which are currently available from the American Type Culture Collection (ATCC, Manassas, Va.), or from any other serotype of adenovirus available from any other source. For instance, an adenovirus can be of subgroup A (e.g., serotypes 12, 18, and 31), subgroup B (e.g., serotypes 3, 7, 11, 14, 16, 21, 34, and 35), subgroup C (e.g., serotypes 1, 2, 5, and 6), subgroup D (e.g., serotypes 8, 9, 10, 13, 15, 17, 19, 20, 22–30, 32, 33, 36–39, and 42–47), subgroup E (serotype 4), subgroup F (serotypes 40 and 41), or any other adenoviral serotype. Non-group C adenoviral vectors are discussed in U.S. Pat. Nos. 5,837,511 and 5,849,561 and International Patent Applications WO 97/12986 and WO 98/53087. Preferably, the viral vectors of the library are adenoviral vectors, and the adenoviral genome is isolated from a subgroup C adenovirus, more preferably Ad2 or Ad5.

In certain embodiments, it may be advantageous that the viral vectors that make up the library of viral vectors are deficient in at least one gene function required for viral replication. For example, deletion or disruption of particular regions of the adenoviral genome results in "replication-deficient" adenoviral vectors. In this regard, the adenoviral vector genome can lack all or part of the E1 region and/or all or part of the E2 region, and/or all or part of the E4 region. With respect to the E1 region, the adenoviral vector can be deficient in at least part of the E1a region and/or at least part of the E1b region. In addition, the adenoviral genome can lack all or part of E3 region. Removal of the E3 region does not impact on the ability of an adenoviral vector to replicate. Still, removal of the E3 region allows additional room for insertion of non-native nucleic acid sequences. Adenoviral vectors lacking one or more gene functions required for viral replication in each of two or more regions are said to be "multiply-deficient." Multiply-deficient viral vectors are particularly useful in the present invention in that such vectors can accept large inserts of exogenous DNA. Indeed, adenoviral amplicons, an example of a multiply-deficient adenoviral vector which comprises only those genomic sequences required for packaging and replication of the viral genome (e.g., at least one terminal repeat and packaging signal), can accept inserts of approximately 36 kb.

Alternatively, it may be advantageous for the viral vectors of the viral vector library to be replication-competent or selectively replication-competent. Several selection strategies for identifying gene products depend on viral amplification in vitro and/or in vivo. For example, in instances wherein an adenoviral vector is internalized and recovery of an adenoviral vector encoding a feature of interest is desired, the library of adenoviral vectors preferably is replication-competent to ensure viral amplification and efficient vector retrieval. Construction of selectively replication-competent adenovirus is easily accomplished by the ordinarily skilled artisan by, for example, linking adenoviral genes necessary for replication to inducible or tissue-specific promoters.

Aside from manipulating the viral genome to block viral replication, the viral genome can be manipulated to tailor the library for a particular screening method, animal model, and the like. For example, the viral genome can be manipulated to alter the specificity or recognition of a virus for a receptor on a potential host cell. For instance, one or more adenoviral coat proteins can be modified, for example, either by incorporation of sequences for a ligand to a cell-surface receptor or sequences that allow binding to a bi-specific antibody (e.g., a molecule with one end having specificity for the fiber portion of the coat protein, and the other end having specificity for a cell-surface receptor (see, for example, International Patent Application WO 95/26412)) or to other blood components. In both cases, the typical virus/cell-surface receptor interactions are preferably abrogated, and the adenovirus is redirected to a new cell-surface receptor by means of its chimeric coat protein. One or more adenoviral coat proteins can be modified to generate vectors deficient in binding to native adenoviral cellular receptors, such as the coxsackie adenoviral receptor (CAR) and/or integrins. Viral coat proteins also can be manipulated to alter the immunogenicity of the virus to avoid a neutralizing immune response.

Alternatively, a targeting element, which is capable of binding specifically to a selected cell type, can be coupled to a first molecule of a high affinity binding pair and administered to a host cell (see, for example, International Patent Application WO 95/31566). Then, an adenovirus coupled to a second molecule of the high affinity binding pair can be administered to the host cell, wherein the second molecule is capable of specifically binding to the first molecule, such that the adenovirus is targeted to the selected cell type. Other suitable modifications to an adenoviral vector are described in U.S. Pat. Nos. 5,559,099, 5,731,190, 5,712,136, 5,770,442, 5,846,782, 5,962,311, 5,965,541, 6,057,155, 6,127,525, and 6,153,435 and International Patent Applications WO 96/07734, WO 96/26281, WO 97/20051, WO 98/07865, WO 98/07877, WO 98/40509, WO 98/54346, and WO 00/15823.

The present invention also contemplates the use of viral vectors comprising regions derived from other viral vectors, so called viral vector chimeras. For instance, it may be advantageous in certain instances to construct a library of adenoviral vectors with the ability to integrate into cellular genomes. Incorporation of one or more adeno-associated viral inverted terminal repeats (AAVITRs) into an adenoviral genome, in conjunction with supplying the AAV rep protein, induces integration of the Ad-AAV chimera into a eukaryotic genome. Therefore, in some instances, the adenoviral genome of the recipient DNA molecule comprises regions derived from other viral vectors.

A library of viral vectors, e.g., a library of adenoviral vectors, preferably comprises or consists of a multiplicity of viral vectors comprising a multiplicity of genetic elements. Any number of individual viral vectors can make up the library of viral vectors. Similarly, the complexity of the library of viral vectors can vary according to the particular embodiment. By "complexity" is meant the number of unique individuals in the library. Preferably, the complexity of the library of viral vectors is 1 to $10^{11}$ particles. More preferably, the complexity of the library viral vectors is 2

(e.g., 3, 5, 10, $10^2$, $10^3$, etc.) to $10^9$ (e.g., 10, $10^2$, $10^3$, $10^4$, $10^5$, $10^6$, $10^7$, $10^8$, or any other integer within the range of 2 to $10^9$) particles.

Each member of the library of viral vectors comprises a first heterologous DNA and a second heterologous DNA. By "heterologous" is meant that the DNA is nonnative to the virus or is native to the virus, but is not located in its native location or position within the viral genome. The first DNA and second DNA can be obtained from any source and in any manner. For example, the DNA can be genomic DNA obtained from a source in nature that has not been genetically modified. The DNA can be genomic DNA that has been modified. The first DNA and/or second DNA also can be obtained from an organism that has been modified to exhibit a particular phenotype. The first DNA and/or second DNA can comprise cDNA or can be synthetically made using routine methods known in the art. If desired, the DNAs of the multi-gene viral library can comprise pieces of larger molecules of DNA fragmented by chemical, enzymatic, or mechanical means, polymerase chain reaction (PCR) products of DNA segments, and the like. The first DNA and/or the second DNA can comprise mutated DNA to obtain optimal diversity in the library of viral vectors.

The first heterologous DNA and second heterologous DNA of the multi-gene viral vector library preferably are operably linked to regulatory sequences necessary for expression of the encoded gene products. For example, preferably, the first DNA and/or the second DNA are operably linked to an inducible promoter. The heterologous DNAs also can be operably linked to species- and/or tissue-specific promoters. A large number of animal species are available for use in functionally evaluating or validating nucleotide sequences. Indeed adenoviral vectors, for example, can infect a wide variety of mammalian cells. However, many useful gene transfer vectors, including adenoviral vectors, are not routinely used in some available models (e.g., mouse, zebrafish, C. elegans, Drosophila, non-human primates, dogs, cats, chickens, sea urchins, starfish, snails, parasites, etc.) because commonly used promoters are not able to express sufficient amounts of gene product in the relevant species or tissue or the expression vector cannot enter the host cell. Expression vectors can be used in a wider array of models if appropriate regulatory sequences (e.g., tissue-specific or species-specific) are incorporated into the vector or if the expression vector is manipulated to include surface ligands that enable entrance into the host cell via cell surface receptors. Also preferably, the first heterologous DNA and the second heterologous DNA can be under the control of separate regulatory elements. Alternatively, the first heterologous DNA and the second heterologous DNA can be under the control of a bi-directional promoter.

Manipulation of the heterologous DNAs can provide a means to detect interaction between the encoded gene products or to purify encoded gene products. For example, the first gene product and/or the second gene product can be fused to a motif at the N- or C-terminus which allows detection or capture of the gene product in a manner not associated with activity of the gene product, i.e., an antibody tag or a his tag (polyhistidine motif). Fusion of an antibody tag to the first or second gene products allows the detection of physical interaction between proteins by the use of immunoprecipitation and mass spectrometry. Alternatively, the first gene product is fused to a DNA binding domain and the second gene product is fused to an activation domain or vice versa. The activation domain (e.g., VP16, etc.) is preferably fused to the C-terminus. In this situation, the infection of cells designed to signal DNA binding using fluorescence indicates protein-protein interactions.

The first DNA and/or the first gene product is preferably known by the investigator, such that meaningful determination of the interaction between the first and second gene products can be accomplished. One of ordinary skill in the art will appreciate that the precise nature or identity of the first gene product will depend on the particular embodiment of the present invention. The first gene product can be, for example, an angiogenic factor, an anti-angiogenic factor, a transcription factor, a growth factor, a cytokine, an apoptotic agent, an anti-apoptotic agent, or a neurotrophic factor. The first gene product also can be a kinase or a phosphatase. If the first gene product is an angiogenic factor, the first gene product is preferably an endothelial mitogen, a factor associated with endothelial cell migration, a factor associated with vessel wall maturation, a factor associated with vessel wall dilation, a factor associated with extracellular matrix degradation, or the like. Most preferably, the first gene product is a vascular endothelial growth factor (VEGF) or pigment epithelial-derived factor (PEDF). If the first gene product is a VEGF, it is preferably a non-heparin binding VEGF, such as $VEGF_{121}$. As used herein, the first gene product, which is common to all the members of the viral vector library, is preferably a factor that is required for a particular screening method to work. For example, when the goal of a screen is to identify factors that enhance angiogenesis in an animal, the first gene product preferably is an angiogenic factor, and enhanced angiogenesis is sought to be detected. In other words, the first gene product is desirably not a marker gene, unless the purpose of the screen is to characterize the functions of marker genes.

In view of the need in the art to identify structurally- or functionally-related gene products and related gene functions centered around a known function, the present invention further provides a method of identifying functionally-related coding sequences using a multi-gene viral vector library. The method comprises culturing a pool of viral vectors, wherein each member of the library comprises a first heterologous DNA encoding a first gene product and a second heterologous DNA encoding a second gene product. The first heterologous DNA is common to each member of the library of viral vectors, while the second heterologous DNA varies between the members of the library of viral vectors. The method further comprises comparing the activity of the gene products encoded by the library of viral vectors with the activity of the first gene product encoded by a viral vector comprising the first heterologous DNA but not comprising the second heterologous DNA. Any biological activity of the gene products can be detected and compared to characterize the gene products.

The multi-gene viral vector library and methods of use thereof provided by the present invention can be employed to identify gene products which, for example, enhance or repress the activity or biological effect of the known gene product. By "functionally-related" is meant gene products that act in concert to produce a biological effect, gene products that are antagonists of each other, gene products that act synergistically to amplify a biological activity, gene products that act at different points of a cellular signal transduction pathway, or the like. Any biological activity can be the basis of screening the viral vector library. For example, when the common gene product is an angiogenic factor, e.g., a VEGF, and the second heterologous DNA encodes a putative angiogenic factor, at least a portion of the library of viral vectors is administered (cultured) in vivo, and enhanced neovascularization is sought to be detected and compared to neovascularization induced by expression of the common gene product alone. Alternatively, the second heterologous DNA encodes a putative neurotrophic factor while the common gene product is a neurotrophic factor. To identify a member of the viral vector library comprising a desirable feature, the ability to enhance the activity of the known neurotrophic factor, at least a portion of the library of viral vectors is administered (cultured) in vivo, and enhanced neuron survival is sought to be detected and compared to neuron survival provided by expression of the common gene product alone. Alternatively, neurons are infected with at least a portion of the library of viral vectors in vitro, neurons are insulted using a variety of techniques, and enhanced neuron survival is sought to be detected and compared to neuron survival provided by expression of the common gene product alone. Contrariwise, the above-described methods also can be utilized to identify factors that repress, not enhance, activity of the common gene product. If desired, the second gene product or the second heterologous DNA, particularly the second DNA that results in the observed desired activity, can be recovered and/or identified.

One of ordinary skill in the art will appreciate the freedom provided by the library and methods described herein to functionally evaluate nucleotide sequences and gene products. Indeed, gene products (as well as the nucleotide sequences that encode them) that physically interact or are functionally-related can be identified. If desired, multiple rounds of screening can be performed to validate results or to further characterize a DNA sequence. For example, the second heterologous DNA can be used in further rounds of screening as the DNA that is held constant throughout the library (e.g., the second DNA becomes the "first" DNA in subsequent screening methods). Entire signal transduction pathways or cascades can be mapped in this manner.

Alternatively, the first gene product can be encoded by a nucleic acid sequence located on an expression vector other than the member of the viral vector library. In this aspect, the method of identifying functionally-related coding sequences preferably comprises co-culturing (a) an expression vector comprising the "first" heterologous DNA and (b) one or more members of the viral vector library. The expression vector can be any suitable vector. Desirably, the expression vector is a viral vector, such as an adenoviral vector or an adeno-associated viral vector. In certain embodiments, the library of viral vectors will be used to infect host cells to select, identify, or characterize a gene product. In this instance, the library of viral vectors and the expression vector are co-administered to the host cell(s). One of ordinary skill in the art will appreciate that "co-administration" of the expression vector includes administration before, concurrently with, e.g., in combination with one or more members of the viral vector library (such as the adenoviral vector library) in vitro or in vivo, in the same composition or in separate compositions, as appropriate, or after administration of one or more members of the viral vector library. In this instance, administration is meant to include both administration to a whole animal and the contacting of individual organs, tissues, or cells with the expression vector and adenoviral vector library. Administration also is meant to include introduction of at least a portion of the viral vector library to cells in vitro. The gene product encoded by the expression vector is constant throughout the screening process, while the viral vector library provides a variable second gene product to identify structurally- or functionally-related gene products, study synergistic or repressive activities of two or more gene products, and the like.

In addition to the multi-gene genetic library, the present invention provides a method of constructing a library of viral vectors. The method comprises carrying out homologous recombination between a first DNA molecule and a second DNA molecule to produce a homologously recombined pool of intermediate viral genomes, wherein the pool of intermediate viral genomes comprises double-stranded DNA. The second DNA molecule is a recipient DNA molecule comprising at least a terminal repeat and packaging signal (used herein as equivalent to "packaging sequence") of a viral genome. The method further comprises ligating one or more linear third DNA molecules into the pool of intermediate viral genomes to produce a library of viral vector genomes, wherein one or more linear third DNA molecules encode(s) a potentially desirable feature. The linear DNA molecules can be the same or different. The library of viral vector genomes is transduced into a first population of host cells to convert the library of viral vector genomes into a library of viral vectors. Preferably, the second DNA molecule comprises a viral genome and the first DNA molecule comprises an expression cassette backbone. Also preferably, the second DNA molecule further comprises an origin of replication, an independent positive selection marker gene, and a dual selection cassette (DSC). The dual selection cassette encodes a positive selection gene product and a negative selection gene product. When the second DNA molecule comprises a dual selection cassette, prior to the ligation reaction, the method preferably further comprises propagating the homologously recombined pool of intermediate viral genomes under conditions wherein the negative selection gene product is active to obtain a selected DNA.

In another embodiment, the present invention provides a method of constructing a library of viral vectors wherein the varying element of the library, the linear DNA molecules, is incorporated into the viral genome via homologous recombination. Accordingly, the method comprises providing linear DNA molecules for incorporation into a viral genome. One or more linear DNA molecules, which can be the same or different, encode(s) a potentially desirable feature. Preferably, the desirable feature is a peptide with at least one desirable activity. Recipient DNA molecules are also provided. The recipient DNA molecules comprise at least a terminal repeat and a packaging signal of a viral genome, an origin of replication, an independent positive selection marker gene, and a DSC. The DSC encodes a positive selection gene product and a negative selection gene product. Preferably, the recipient DNA molecules comprise a viral genome. The method further comprises carrying out homologous recombination between the pool of linear DNA molecules and the recipient DNA molecules to produce a homologously recombined library of viral vector genomes, wherein the library of viral vector genomes comprises double-stranded DNA. The library of viral vector genomes is then propagated under conditions wherein the negative selection gene product is active to obtain a selected DNA. The homologously recombined library of viral vector genomes is then transduced into a first population of host cells to convert the library of viral vector genomes into a library of viral vectors. The present inventive method preferably further comprises selecting a viral vector comprising a desirable feature, which optionally comprises transducing a second population of host cells with the library of viral vectors. The present inventive method can be used for the construction of a library comprising any type of virus, although the method is particularly suited for the construction of an adenoviral vector library.

The linear DNA molecules for use in the present inventive method can be the same, i.e., the linear DNA molecules comprise DNA fragments that encode the same peptide or functional nucleic acid sequence or variations thereof, or different, i.e., the linear DNA molecules comprise DNA fragments that encode different peptides or functional nucleic acid sequences. One or more linear DNA molecules are incorporated into the recipient DNA molecules to construct a library of viral vector genomes. Optionally, two or more linear DNA molecules are incorporated into the recipient DNA molecules, for instance, to determine the interaction of two potentially desirable gene products. One of ordinary skill in the art will appreciate that the method of constructing a library of viral vectors provided herein is suitable for the construction of multi-gene libraries as well as single gene libraries. For example, the multi-gene viral library of the present invention can be constructed by using recipient DNA molecules comprising the first heterologous DNA or by ligating into the viral genomes linear DNA molecules comprising the first heterologous DNA (as "first heterologous DNA" is described herein).

The linear DNA molecules can be obtained from any source and in any manner. For example, a pool of linear DNA molecules can be genomic DNA obtained from a source in nature that has not been genetically modified. The linear DNA molecules can be genomic DNA that has been modified. The linear DNA molecules also can be obtained from an organism that has been modified to exhibit a particular phenotype. The linear DNA molecules can comprise cDNA or can be synthetically made using routine methods known in the art. No matter the source, the linear DNA molecules can be of any size so long as, when inserted into the recipient DNA molecules, the viral vector genomes can be converted into viable viral particles. If required, linear DNA molecules can comprise pieces of larger molecules of DNA fragmented by chemical, enzymatic, or mechanical means. Linear DNA molecules also can comprise polymerase chain reaction (PCR) products of DNA segments, and the like. Preferably, the linear DNA molecules are obtained from a population of DNA comprising a multiplicity of genetic elements.

Each linear DNA molecule can encode a potentially desirable feature. Optionally, the DNA fragment of the linear DNA that encodes the desirable feature is mutated in order to obtain a pool or collection of linear DNA molecules encoding peptides or functional nucleic acid sequences with varying properties. The probability of identifying a peptide or functional nucleic acid with a desired activity depends greatly on the diversity of the genetic library. It is, therefore, advantageous to mutate the linear DNA molecules to obtain optimal diversity in the library of viral vectors. DNA molecules can be mutated using numerous methods well understood in the art, such as, for example, exposure to mutating chemical agents, e.g., ethidium bromide, in vitro mutagenesis such as recursive shuffling (see, for example, International Patent Application WO 98/13485), error-prone PCR, error-prone transcription, and the like. However, mutation of the linear DNA molecules is not required. When screening genomic libraries to associate a function with a nucleotide sequence, for example, the linear DNA molecules are preferably not mutated.

The desirable feature encoded by the linear DNA can be any gene product, such as a peptide or functional nucleic acid sequence. Preferably, the desirable feature encoded by the linear DNA molecules is a peptide comprising at least one desirable activity. As used herein, "peptide" refers to an amino acid sequence of any length. Therefore, "peptide" is meant to encompass peptides, polypeptides, proteins, and fragments thereof. Preferably, the linear DNA molecule or surrounding viral genome comprises regulatory sequences necessary for expression of the peptide, such as a promoter. Alternatively, the recipient DNA molecule can comprise regulatory sequences positioned such that the nucleic acid sequence encoding the potentially desirable feature, e.g., a peptide, is operably linked to the regulatory sequences. The desirable activity will depend upon the particular embodiment of the present inventive method and can be any detectable biological activity. A desirable activity can be, for example, specificity for a given ligand or receptor; the ability to regulate an enzyme or an ion channel; the ability to trigger a signal transduction pathway; the ability to stimulate a physiological response; toxicity to a host cell; the ability to inhibit cellular responses, cell motility, macromolecule synthesis, macromolecule degradation, complement activation, or complement deactivation; the ability to mimic a given factor, e.g., a neurotransmitter; the ability to stimulate or inhibit cell proliferation; bactericidal, fungicidal or anti-parasitic activity; the ability to stabilize an adenoviral vector or alter gene expression; the ability to avoid neutralization of adenovirus; the ability to avoid innate clearance mechanisms in vivo; or the like.

Although it is preferred that the linear DNA molecules comprise DNA fragments encoding a peptide, the linear DNA molecules can encode a functional nucleic acid sequence. By "functional nucleic acid sequence" is meant a nucleic acid sequence, i.e., DNA or RNA, that performs a function or has an activity within a cell. An example of a functional nucleic acid is antisense RNA that impedes transcription or translation of a DNA or RNA sequence. Functional nucleic acid sequences also include, but are not limited to, promoters, enhancers, enzyme binding sites, splice sites, and ribozymes.

The linear DNA molecules described herein are incorporated into recipient DNA molecules comprising at least a terminal repeat and packaging signal of a viral genome. Of course, one of ordinary skill in the art will appreciate that the recipient DNA molecules need not comprise an entire, intact viral genome. Recipient DNA molecules can comprise a portion of the viral genome, preferably a portion comprising genomics sequences responsible for replication of the viral genome (terminal repeats) and packaging of the virus (packaging signal). Terminal repeats and packaging signals are well understood in the art and are further described in, for example, Shinagawa et al., *Gene*, 55, 85 (1987). For example, regions of the viral genome can be deleted to produce replication-deficient vectors. Indeed, the viral backbone can be modified to produce a library of recombined viral vectors tailored to a particular screening method. Preferably, the recipient DNA molecules comprise all or part of an adenoviral genome. A discussion of adenoviral vectors and suitable modifications of the adenoviral genome is provided herein. The adenoviral genome of the recipient DNA molecule can be derived from any adenovirus. The recipient DNA molecules can further comprise a phage packaging site, an origin of replication, an independent positive selection gene, and/or a dual selection cassette.

Preferably, the recipient DNA molecules comprise a phage packaging site, such that packaging the library of adenoviral vector genomes into phage capsids prior to converting the library of viral vector genomes, e.g., the library of adenoviral vector genomes, into a library of viral vectors (cosmid cloning) is possible. The phage packaging site can originate from any phage, but must incorporate double-stranded DNA into the corresponding phage capsid.

The phage packaging site is chosen, in part, to accommodate the size of the recipient DNA molecule with the inserted linear DNA molecule. For example, T7 capsids package a smaller nucleic acid molecule than lambda capsids. Therefore, if a T7 packaging site is incorporated into the recipient DNA molecule, then a smaller vector can be efficiently packaged into the relatively smaller capsid of T7. In contrast, if a lambda packaging site is incorporated into the recipient DNA molecule, then the lambdid vector can be much larger without substantially reducing the efficiency of packaging. The lambda packaging site, cos, is among those phage packaging sites preferred in the context of the present invention.

The packaging site also can be selected to comport with the use of particular phage coat proteins. For example, chimeric T7 coat proteins having affinity for eukaryotic cells can be made. If it is desired to package the present inventive vector into a capsid comprising such a chimeric T7 coat protein, then it is preferable to use a T7 packaging site in the recipient DNA molecule. Similarly, incorporation of a chimeric lambda protein dictates that the present inventive vector comprises a lambda packaging site.

Preferably, with respect to adenovirus, the recipient DNA molecule is configured such that the phage packaging site is proximal to an adenoviral ITR. Such a configuration allows for direct generation of an amplicon when the library of adenoviral vector genomes is transduced into a suitable complementing cell. This is true because many phage linearize DNA to be packaged and because if an ITR or long terminal repeat (LTR) is suitably proximal to a free terminus of a DNA that comprises an adenoviral vector genome, and that linear DNA is delivered to a mammalian cell permissive for the production of the adenoviral vector, then replication of the library of adenoviral vector can occur. By proximal, it is meant within about 250 base pairs, preferably within about 100 base pairs, and more preferably within about 25 base pairs. In other words, proximity of an ITR or LTR to a packaging site allows for the replication of the library of adenoviral vector in a mammalian cell without the need to linearize or cut the DNA with restriction enzymes prior to introduction into the mammalian cell.

The recipient DNA molecules comprising a viral genome and, optionally, a phage packaging site can be generated using any number of vector construction strategies that employ standard techniques, such as those techniques known in the art. In one embodiment, for ease of construction, the recipient DNA molecule is preferably generated to comprise at least part of a viral genome comprising a generic expression cassette backbone that allows easy insertion of linear DNA molecules into a region of the viral genome. Such a generic viral backbone enables assembly of a library of viral vector genomes in a single reaction. An expression cassette backbone is a DNA fragment that comprises the necessary elements for the insertion and expression of the linear DNA molecules. The expression cassette desirably comprises a unique restriction site for ligation of the linear DNA into the viral genome. Preferably, the expression cassette further comprises a promoter and, optionally, transcription termination sequences, as well as other elements useful in peptide expression.

Furthermore, the recipient DNA molecule and/or the linear DNA molecule can comprise other genetic elements that facilitate construction of the library and/or removal of a relevant coding sequence. For example, the recipient DNA molecule and the linear DNA molecule can comprise site-specific recombination sites such that, upon recombination, the linear DNA is inserted into the recipient DNA molecule to create a library of adenoviral vector genomes. Optionally, the genomes can then be cosmid-cloned, as described herein, to create a library of adenoviral vector genomes. The presence of site-specific recombination sites is particularly useful for rescuing all or part of the linear DNA molecule of interest. A gene transfer construct comprising acceptor recombination sites can be used in a post-screening recombination event to isolate the linear DNA from the library for subsequent screening or characterization.

Recombinant viral vectors are most often made via homologous recombination. Procedures and systems described in the art allow relatively rapid production of recombinant eukaryotic viruses. However, previously described methods lack the flexibility and suitable selection pressures to efficiently generate the viral backbones, in particular the adenoviral backbones, that eventually constitute the library of viral vectors. Especially preferred methods of generating a recipient DNA molecule are described in International Patent Applications WO 98/56937 and WO 99/15686. For example, the recipient DNA molecule preferably comprises a viral genome into which is inserted an expression cassette backbone comprising at least one unique restriction enzyme site flanked by sequences necessary to drive expression of any linear DNA molecule inserted into the unique restriction enzyme site. Such an expression cassette can be introduced into a region of a viral genome via homologous recombination. In a preferred method of recipient DNA molecule construction, an intermediate DNA molecule is generated, which comprises a viral genome, an independent positive selection marker gene, an origin of replication, a dual selection cassette located within the viral genome, and at least one of the following: one or more unique restriction enzyme sites (URES) or one or more flanking site-directed homologous recombination sites. Preferably, the intermediate DNA molecule, and, subsequently, the recipient DNA molecule, further comprises a phage packaging site. By "independent positive selection marker gene" is meant a positive selection gene, as described below, which is not part of a dual selection cassette. The dual selection cassette (DSC) contains at least six genetic elements (or functional DNA segments) which can (but need not) overlap each other and include (i) a first and (ii) a second viral vector homology region, (iii) a DNA encoding a negative selection gene product that is operably linked to (iv) a negative selection gene promoter, and (v) a DNA encoding a positive selection gene product that is operably linked to (vi) a positive selection gene promoter. A DNA encoding a selection gene product operably linked to a promoter is a "selection gene." The identity of the first and second homology regions are independently selected, and are of sufficient size and homology so as to enable a homologous recombination event with a portion of a viral genome, or an analog thereof, such that a desired region of a virus, viral vector, or analog thereof, is replaced (or modified) as a result of the homologous recombination event as described below. The first and second homology regions are separated by the negative and positive selection genes of the DSC.

By "negative selection gene product" is meant any RNA or protein that can confer a strong growth disadvantage to a host expressing it, preferably causing the death of a host expressing it, under appropriate conditions. Examples of negative selection gene products include, but are not limited to, NP-1, sacB, products of the ccd genes (e.g., ccdB), products of a tetracycline resistance gene ($tet^R$), products of the par genes (e.g., parD), Kid, and the OmpA FLAG/NP-1 fusion protein. Preferably, the negative selection gene product is inducible, i.e., the DNA encoding the negative selection gene product is operably linked to an inducible negative selection gene promoter. By "positive selection gene product" is meant any RNA or protein that will confer a growth advantage to a bacterium carrying a DNA molecule comprising the positive selection gene under a particular and known condition. Exemplary of a positive selection gene product is the gene product of the zeocin resistance gene, ble. The independent positive selection marker gene can also encode a factor that will confer a growth advantage to a bacterium carrying the vector. However, the independent positive selection marker gene can alternatively encode a detectable gene product or marker peptide, such as green fluorescent protein (gfp) or the luciferase enzyme. Optionally, a single gene can function as both a positive and negative selection gene in the dual selection cassette, depending upon the promoter. For example, a DSC comprising an EM-7 promoter and encoding a zeocin resistance protein or encoding a lacZ-zeocin resistance fusion protein can be incorporated into the intermediate vector. The dual selection cassette can be introduced into the viral genome by a variety of methods, although homologous recombination is most preferred.

Following transfection of a nucleic acid sequence encoding a DSC flanked by regions of homology to a viral genome and a starter plasmid comprising a viral genome, an independent positive selection marker gene, and, optionally, a phage packaging site, a dual recombination event occurs, and colonies comprising the intermediate DNA molecule can be selected according to resistance conferred by both the independent positive selection marker gene and the positive selection gene of the dual selection cassette. Additional description of a dual selection cassette is set forth in International Patent Application WO 99/15686.

To construct the desired recipient DNA molecule, the intermediate plasmid and a donor plasmid comprising the expression cassette backbone flanked by regions homologous to the DNA sequences flanking the dual selection cassette are transfected into a bacterial host, wherein enzymes provided within the host mediate two homologous recombination events. The host is maintained for a suitable period of time (e.g., 2–24 hours) under conditions that are selective for the independent positive selection gene. Thereafter, the transformed bacterial host is grown under conditions such that the negative selection gene promoter becomes active (i.e., the negative selection gene promoter is induced and/or depressed, or, alternatively, when a constitutive promoter is used for the negative selection gene promoter, a substrate for the negative selection gene product is added to the growth medium or substrate). Individual viable cells are then isolated, propagated, and screened for the desired recipient DNA molecule. Identifying individual cell isolates comprising the desired recipient DNA molecule by standard techniques is vastly simplified in comparison to prior art techniques (for constructing and identifying a desired construct), in that the resultant bacterial colonies must harbor the independent positive selection gene and must not harbor the negative selection gene of the dual selection cassette. A preferred recipient DNA molecule comprises the expression cassette backbone comprising at least one unique restriction enzyme site surrounded by sequences necessary for transcription of any linear DNA molecule inserted at the restriction enzyme site. One of ordinary skill in the art will appreciate that many other vector construction strategies exist for generating recipient DNA molecules for use in the present inventive method, and the linear DNA molecules can be inserted anywhere in the adenoviral genome.

The present inventive method of constructing a library of viral vectors comprises ligating linear DNA molecules into recipient DNA molecules. Numerous kits are commercially available which enable digestion and ligation of DNA molecules. For a discussion of restriction digestion and ligation of DNA molecules, see, for example, Sambrook et al., *Molecular Cloning, a Laboratory Manual,* 2nd edition, Cold Spring Harbor Press, Cold Spring Harbor, N.Y. (1989), and Ausubel et al., *Current Protocols in Molecular Biology,* Greene Publishing Associates and John Wiley & Sons, New York, N.Y. (1994). Numerous methods of ligating the linear DNA molecules into the recipient DNA molecules are available, and the viral genome can be manipulated to accommodate the insertion of the linear DNA molecule if needed. For example, the adenoviral genome can be made deficient in the Sfi I restriction site. The Sfi I restriction enzyme (Clonetech Laboratories, Palo Alto, Calif.) can then be used to ligate a linear DNA molecule into the pool of adenoviral vector genomes.

In an alternative embodiment, one or more linear DNA molecules is provided, wherein at least one linear DNA molecule encodes a potentially desirable feature. If desired, a pool or collection of linear DNA molecules is provided. Recipient DNA molecules are also provided. The recipient DNA molecules comprise at least a terminal repeat and packaging signal of a viral vector genome, an origin of replication, an independent positive selection marker gene, and a dual selection cassette, all of which are described herein. The linear DNA fragments are flanked by regions homologous to DNA sequences flanking the dual selection cassette of the recipient DNA molecules. The method further comprises carrying out homologous recombination between the linear DNA molecules and the recipient DNA molecules to produce a homologously recombined library of viral vector genomes, wherein the library of viral vector genomes comprises double-stranded DNA. Preferably, to carry out homologous recombination, the linear DNA molecules and the recipient DNA molecules are transfected into a bacterial host, wherein enzymes provided within the host mediate two homologous recombination events. The bacterial host cells are maintained for a suitable period of time (e.g., 2–24 hours) under conditions that are selective for the independent positive selection gene. Thereafter, the transformed bacterial host is grown under conditions such that the negative selection gene promoter becomes active and viable cells are isolated, propagated, and screened for the desired adenoviral vector genomes. As stated above, the use of a DSC in the methods of constructing a viral vector library of the present invention are superior to previously described methods of library construction by, for example, providing an enhanced means of selecting members of the library of viral vector genomes.

The recipient DNA molecules comprising linear DNA molecule inserts form a library of viral vector genomes. One of ordinary skill in the art will appreciate that the viral genomes need not comprise the entire, intact genome. The vectors of the library can comprise partial viral genomes if desired. Incorporation of a phage packaging site into the recipient DNA molecule enables packaging of the library of adenoviral vector genomes into phage heads in vitro or in vivo and subsequent transduction of bacterial cells (cosmid cloning). Cosmid cloning is a convenient method of generating highly complex libraries of large DNA molecules. Preferably, the library of viral genomes is packaged as double-stranded DNA into lambda capsids. Cosmid cloning using lambda phage elements is superior to cloning methods using other phages, such as M13. The packaged genetic material is more stable, greater amounts of genetic material can be packaged, and insert sizes can be predetermined and designed when working with lambda phage, as opposed to M13. The library of viral vector genomes is packaged as double stranded DNA. Double stranded DNA is more stable than single stranded DNA, thereby increasing the probability that intact, viable virus particles will be produced by the present inventive method. The packaged library of viral vector genomes can efficiently transduce and be propagated in bacterial cells as plasmids. In a standard cosmid cloning reaction, $10^5$ to $10^6$ individual clones are generated.

If desired, the library of viral vector genomes can be produced or stored in an array format. For instance, each bacterial colony, which comprises a single clone of the library, can be isolated and converted to an array format on culture plates or multi-well plates to facilitate cataloging and archiving of the library. Moreover, use of an array format facilitates conversion of a subpopulation of the library for screening as may be required when working with highly complex libraries. The conversion can be of one or more genomes at a time or a mixture of one or more genomes. One hurdle involved in screening genetic libraries is correlating a desired result with a nucleotide sequence responsible for that result. By producing, converting, or storing the library of viral vectors in an array format, the ordinarily skilled artisan can correlate a biological effect to a single viral clone and, optionally, identify the relevant coding sequence.

Conversion of the library of viral vector genomes into a library of viral vectors can be accomplished by transducing a first population of host cells that support virus production with linearized DNA harvested from the bacterial cells. For example, adenoviral DNA can be isolated from bacterial cells, purified, and transduced into cells that support adenovirus production using routine techniques known in the art. Methods of introducing DNA into a cell are numerous and include, for example, transfection, electroporation, microinjection, and microprojectile bombardment (see, for example, Sambrook et al. and Ausubel et al., supra). To ensure efficient conversion, preferably at least one of the viral terminal repeats (e.g., inverted terminal repeats, ITRs) present in the adenoviral genome is free of the plasmid backbone. One of ordinary skill in the art will appreciate that the entire library, e.g., each reaction product, need not be converted but, instead, subpopulations of the library of viral genomes can be converted to a library of viral vectors. A cell that supports virus production can be any cell that allows production of virions or viral particles from an adenoviral vector genome. In embodiments wherein the viral vector is deficient in at least one gene function required for viral growth or reproduction, the necessary gene functions must be supplied in trans. A number of complementing cell lines comprising various regions of viral genomes integrated into the cellular genome exist and are routinely used to produce replication-deficient viral vectors such as replication-deficient adenoviral vectors. Commonly used complementing cell lines include Per.C6, 293, 911, lung carcinoma-derived cell lines (e.g., A549-derived cell lines), and the like. The transduced cells are maintained using routine cell culturing techniques to produce a library of viral vectors, which subsequently can be harvested and purified. Exemplary methods of harvesting and/or purifying viral vectors, in particular adenoviral vectors, are discussed in International Patent Application WO 99/54441.

Optionally, in instances wherein the library of viral vector genomes is cosmid-cloned, the phage capsids can be modified to infect complementing cell lines. Alternatively, the complementing cell lines can be transfected with the phage/viral genome DNA. Thus, the viral vector genome need not be isolated from the phage DNA prior to transduction of a complementing cell line. However, a restriction enzyme is required within the complementing cell to nick or cut the DNA such that efficient conversion of the genomes to viable viral particles occurs.

The first population of host cells need not be "complementing" cells in the sense that the cellular genome comprises nucleotide sequences encoding factors required for viral replication. The required factors can be provided in trans by a helper virus. For example, the genome of an adenoviral amplicon is transduced into a first population of host cells. The host cells also are contacted with a helper adenovirus that complements the factors necessary for replication of the amplicon. The amplicon and helper virus are harvested, and measures are taken to separate the amplicon from any contaminating helper virus to produce a library of adenoviral amplicons. One of ordinary skill in the art will appreciate that helper viruses can be used to convert other types of viral genomes to viral vectors in addition to adenoviral amplicons.

In one embodiment, the library of viral vector genomes is a library of adenoviral vector genomes, wherein the viral vector genomes are deleted or disrupted in one or more essential regions for viral replication (i.e., the E1a region). The library of adenoviral vector genomes are transduced into a suitable complementing cell line such that the complementing cell line provides in trans the factors required by the adenoviral vector to produce viable viral particles. To increase the efficiency of conversion of the viral genomes to viral particles, the complementing cell line is infected with a helper adenovirus that is deficient in at least one additional region of the adenoviral genome required for viral growth that is not provided in trans by the complementing cell line. For instance, if the members of the library of adenoviral vector genomes are E1-deficient, the helper adenovirus is E1- and E4-deficient and the complementing cell line complements E1-deficiencies only. The helper adenovirus provides accessory factors which facilitate conversion of adenoviral genomes to viable adenoviral particles. Since the complementing cell line is unable to complement the helper adenovirus, no contamination of the library with helper virus will occur.

The present invention also provides methods of using viral vector libraries. Preferably, the present inventive method further comprises selecting a viral vector comprising or encoding a desirable feature. Optionally, the viral vector of interest can be isolated from a sample using routine techniques. If the desirable feature is a peptide comprising a desired activity, the peptide can be isolated and/or identified. Also, the linear DNA molecule encoding the desirable feature is identified. Isolation and characterization of nucleic acids is well known in the art. Optionally, selecting a viral vector comprising a desirable feature comprises isolating the library of viral vectors from the first population of host cells and transducing a second population of host cells in vitro or in vivo with the isolated library of viral vectors or a subset thereof, although many of the screening methods described herein can be accomplished within the first population of host cells. In some embodiments, the method of the present invention comprises isolating the library of viral vectors from the first population of host cells and administering the library of viral vectors to an animal, such as a mouse or a human. An entire library of viral vectors or a subset of the library can be administered to an animal or introduced into cells in vitro or in vivo. Alternatively, the sublibrary comprising a population of identical viral vectors, a library comprising a complexity of 1, can be introduced into an individual cell or animal. In other words, different single viral vector clones can be administered to different individual animals to select a viral vector comprising or encoding a desirable feature. Optionally, when a library of viral vectors is administered to an animal, a second population of host cells is transduced in vivo.

Indeed, the methods of using a library of adenoviral vectors described herein can be performed in vivo. The skilled artisan will appreciate the utility of the present inventive method in screening genomic libraries, in particular muti-gene libraries, in vivo and screening for therapeutic factors. Most previously described methods of screening nucleic acid sequences comprise in vitro expression of encoded gene products. The expressed gene product is either identified in vitro, or administered as a peptide in vivo. The method of using a library of viral vectors described herein is superior to previously described methods by efficiently delivering at least one linear DNA molecule encoding a putative peptide or functional nucleic acid to a cell in vivo, wherein the gene product is expressed. The putative peptide or functional nucleic acid comprising a desirable activity can be identified by screening for a function in vivo. The in vivo model for screening the library of viral vectors depends on the desired feature. In one aspect, the library of viral vectors is administered to a diseased animal in order to select for a viral vector comprising a therapeutic factor. Of course, animal models of a number of diseases and disorders are available for use in the present inventive method. It is also appropriate to administer the library of viral vectors to a healthy animal to observe any change in phenotype in a wild-type animal in response to delivery of the linear DNA molecules. In another aspect, the library of viral vectors is administered to a transgenic or knock-out animal. A viral vector that complements the missing function then can be identified. Alternatively, the library of viral vectors is administered to an animal to induce a physiological response, and the viral vector comprising a desirable feature is not selected from the library. Selecting the viral vector comprising a desirable feature in vivo does not require transduction of a second population of host cells. For example, when the desirable feature is an increased half life in blood circulation, decreased clearance from the body, or decreased inactivation or degradation of the vector in vivo, the library of viral vectors is preferably not taken up by host cells in the animal. The members of the library of viral vectors can be manipulated by, for example, manipulation of the viral coat protein, to diminish their ability to bind and enter host cells, if desired.

In some embodiments, selecting a viral vector comprising a desirable feature involves a multiple step process wherein a particular change in the phenotype of the transduced cell or infected animal is observed, such as cell survival under normally lethal conditions, expression of a nonnative gene product, changes in the environment harboring the cell (in vitro or in vivo), etc. The product encoded by the nucleic acid sequence of the linear DNA molecule can potentially alter the expression of endogenous genes, trigger or block signal transduction pathways, or cause an accumulation of metabolic byproducts, all of which are detectable by the skilled artisan. Conversely, a change in the phenotype of the virus comprising the linear DNA molecule(s) encoding a desired feature is observed. In another aspect, the library of viral vectors is introduced into an animal in vivo to select for a viral vector comprising a desirable feature. In any case, optionally, the linear DNA molecules encoding the gene product can be identified, and its DNA sequence elucidated. Similarly, if desired, the encoded peptide can be identified. The present invention is quite powerful in associating a function with a gene product or a nucleic acid sequence and screening for functionally-related coding sequences. Set forth below is a discussion of particular embodiments of the present invention, which should not be construed to limit the scope of the present invention in any way.

The present inventive method has particular utility in identifying nucleic acid sequences encoding viral peptides, especially adenoviral peptides, with a desirable activity. It should be noted that aside from simply identifying peptides and linear DNA molecules encoding peptides with a particular function, it is also possible to use a library of viral vectors (e.g., adenoviral vectors) to identify DNA molecules encoding peptides with superior activity compared to wild-type viral peptides. In addition, the peptides with a desired activity, as used herein, need not be peptides found in nature. Novel peptides having altered properties and activity compared to wild-type peptides can be generated by mutation of DNA molecules encoding a known peptide or functional nucleic acid. With respect to viral peptides, use of a library of viral vectors allows screening of viral peptides or functional nucleic acid sequences in their natural environment. In contrast, viral peptides identified through the use of plasmid or phage expression libraries require an additional round of selection in a viral vector to confirm the function of the peptide. In some instances, peptides expressed by phage do not comprise the same properties when expressed from a viral vector such as an adenoviral vector (see, for example, Wickham et al., *J. Virol.*, 71, 8221–8229 (1997)). Furthermore, use of a library of viral vectors enables isolation of a final, desired viral delivery vehicle from the selection, whereas additional vector construction would be required using phage display libraries.

A library of viral vectors can be constructed that comprises a multiplicity of genetic elements encoding any viral peptide, such as a putative viral complementation factor. Viral complementation factors are peptides that complement deficiencies in viral vectors due to deletions or mutations in the viral genome. For example, as discussed above, genes located in the early region of the adenoviral genome are oftentimes removed in order to render the virus replication-deficient. Replication-incompetent viruses are considered safe for in vivo use. However, the deleted gene products must be present to propagate the virus in cell culture to obtain a sufficient stock of virus for later use. One of ordinary skill in the art will appreciate that a library of adenoviral vectors comprising putative virus complementation factors is a powerful tool to identify novel functional viral complementation factors or viral complementation factors that better complement virus compared to commonly used, wild-type complementation factors. In this embodiment, the linear DNA molecules encode a putative virus complementation factor and the viral vectors of the library of viral vectors are replication-deficient. For example, the library of adenoviral vectors is transduced into a second population of host cells that do not naturally complement replication-deficient adenovirus. Therefore, in order for the transduced second population of host cells to support the replication of the replication-deficient adenovirus, the adenoviral vector comprises a linear DNA molecule encoding a functional virus complementation factor. Selecting the adenoviral vector with the desirable feature comprises identifying the adenoviral vector capable of replicating, i.e., by maintaining the transduced second population of host cells and observing and quantifying plaque formation or determining the titer of virus after a predetermined time period. Identification of the putative viral complementation factor and its corresponding nucleic acid sequences allows further capitalization of the products encoded by the library of viral vectors. For example, a complementing cell line can be produced by isolating the linear DNA molecule encoding a functional virus complementation factor and stably transducing cells with the linear DNA molecule encoding the functional virus complementation factor. Such a complementation cell line is provided by the present invention. Following this approach, cell lines can be generated to complement virtually any viral deficiency. In addition, cell lines can be generated that better complement deficient virus compared to currently used complementation cell lines.

Aside from identifying viral complementation factors, the present inventive method also can be utilized to identify other peptides, such as ligands and cellular receptors that mediate entry into a host cell. As used herein, a cellular receptor is a peptide that binds a ligand, such as an adenoviral knob protein. Some cellular receptors mediate entry into the cell. One of ordinary skill in the art will appreciate that subunits of a receptor, or cellular receptor peptides, also can mediate binding of a ligand and, optionally, entry into a cell. The interaction of cellular receptors and ligands on a viral surface is crucial for viral infection to occur. Viruses are known to infect a wide variety of cells. Adenovirus, in particular, infects a wide variety of eukaryotic cells. Still, genetic research and therapy would benefit from the identification of novel cellular receptors or the identification of cellular receptors that, for example, bind more tightly or specifically to a virus. Identification of new receptors would prove useful in both research and clinical settings. For example, in some disease states, antibodies produced by the body recognize and bind cellular receptors, thereby rendering the cells not available for delivery of therapeutic peptides via viral vectors. However, cells previously not recognized by a viral vector can be stably transduced to express a novel cellular receptor in order to facilitate viral infection of those cells for purposes of gene delivery.

To identify a cellular receptor, a library of viral vectors comprising linear DNA molecules encoding a putative cellular receptor peptide is transduced into a second population of host cells. The transduced second population of host cells then is contacted with a second virus that does not infect the cells prior to transduction with the library (i.e., the second virus does not naturally infect the second population of host cells). The virus may not naturally comprise a ligand for the particular cell type, or may comprise mutated ligands not naturally recognized by the transduced cells. The present inventive method preferably further comprises identifying the linear DNA molecule encoding the cellular receptor peptide. In most cases, one of ordinary skill in the art need only to identify the cells that are successfully infected by the second virus to determine which putative cellular receptors are functional and then identify the corresponding linear DNA molecules. Once identified, the linear DNA molecules encoding the functional cellular receptor can be used to generate cell populations that recognize a particular virus that does not naturally infect that cell population. Such cell populations are useful in research and gene therapy practices.

The present inventive method also is particularly useful for identifying ligands, in particular ligands expressed on the viral surface, that, for example, interact with cellular receptors to mediate entry into a host cell. In this aspect, the linear DNA molecules encode a putative ligand. The putative ligand can bind a cellular receptor and mediate entry of the virus into the host cell. Alternatively, the ligand binds an extracellular factor, such as, for example, a secreted protein or carbohydrate, or other soluble molecule. A ligand also can be identified that binds to an immobilized molecule. The immobilized molecule can be used to generate a novel method of purifying viral vectors. Therefore, when the linear DNA molecules encode a putative ligand, selecting the viral vector comprising the desirable feature comprises contacting the ligand with the predetermined molecule, wherein binding of the ligand to the predetermined molecule is detectable, and detecting binding of the viral vector to the predetermined molecule, e.g., a cellular receptor, soluble molecule, immobilized molecule, and the like. When the ligand binds a cellular receptor, the library of viral vectors expressing the putative ligand is contacted with the cellular receptor, which is optionally present on a cell, and binding of the ligand to the cellular receptor is detected. Binding of the ligand to a predetermined molecule, e.g., a cellular receptor, must be detectable. In one embodiment, the cells comprising the cellular receptor and that are exposed to the ligand can be cells that do not naturally recognize the ligand or are not naturally infected by the virus. Alternatively, the putative ligand binds a cellular receptor and enables more efficient viral infection than wild-type virus that do not express the putative ligand.

Detecting binding of the viral vector, e.g., the adenoviral vector, comprising the putative ligand to a cell comprising the cellular receptor can be accomplished by detecting viral infection of the cell or coupling of the ligand to a detectable molecule. When the putative ligand binds an extracellular predetermined molecule, the library of viral vectors is exposed to the predetermined molecule, and binding of the ligand to the predetermined molecule is detected. Optionally, selecting the viral vector comprising a desired feature comprises multiple rounds of screening. For example, a virus comprising a ligand that binds a cellular receptor more efficiently than wild-type virus is harvested from a cell population. Repeated rounds of infection, isolation, and amplification of the adenovirus will enrich the population of harvested virus for viral vectors comprising the desired ligand. Incorporation of a nonnative viral surface protein or other peptide ligand onto the viral surface (i.e., the adenoviral fiber, hexon, pIX, pIIa, pVI, or the penton base) expands the repertoire of potential host cells that are infected by an adenovirus. Alternatively, a virus can be manipulated to target a particular cell population.

In some of the embodiments described above, two separate viruses are employed to identify cellular receptor peptides. However, the use of two separate viruses is not required to identify a receptor or ligand. In some instances, the ligand recognized by a desired receptor is known, thereby greatly facilitating the screening for the desired receptor. In this particular embodiment, the linear DNA molecules encode a putative cellular receptor peptide, wherein the cellular receptor peptide recognizes a predetermined ligand. In terms of virus research, virus surface proteins can be constructed that bind to cellular receptors not normally recognized by that virus. When the ligand to a receptor is known, selecting the viral vector with the desirable feature comprises transducing a second population of host cells with the library of viral vectors and contacting the transduced second population of host cells with the predetermined ligand, wherein binding of the predetermined ligand to the cell surface receptor is detectable. Binding of the cell surface receptor to the predetermined ligand is then detected in cells that express a functional cellular receptor. The study of receptors, in general, is an advanced field of study. Many techniques have been developed to detect binding of a receptor to a ligand. For example, the receptor is expressed on the cell surface and is linked to an ion channel, which opens or closes in response to binding of the receptor to the predetermined ligand. Detection then comprises observing a change in voltage across the cell surface. Alternatively, the receptor is linked to an enzyme, which induces the formation of a detectable gene product upon binding of the receptor to the predetermined ligand. If the receptor is not amenable to coupling with a means of detection, the predetermined ligand can be coupled to a means of detection, such as a marker protein, or a molecule that allows detection by fluorescence activated cell sorting (FACS). After the transduced cells are contacted with the predetermined ligand, any excess ligand is removed. Any detectable marker protein remaining indicates the presence of a functional receptor peptide. FACS, for instance, then can be used to sort cells that express a cellular receptor that binds the predetermined ligand. If desired, the DNA encoding the desired cellular receptor is recovered and analyzed. It should be noted that cellular receptors are not necessarily located on the cell surface. Many cellular receptors of interest are intracellular and can be examined using the present inventive method. In an especially preferred embodiment, the predetermined ligand is an adenoviral knob protein capable of binding a non-native receptor, and the putative cellular receptor peptide is the non-native receptor. The receptors and ligands identified in some of the embodiments described herein can be used to construct targeted viral vectors for use in research and gene therapy.

In addition to the above, the methods of the present invention can be used to identify factors to construct improved viral vectors. Potential limitations associated with any type of expression vector include poor stability, poor infectivity, insert size limitations, poor protein expression, poor tissue or cell specificity, immunogenicity, and toxicity. The methods of using a viral library disclosed herein provide a means to screen viral vectors for improved characteristics. For example, stability of a viral vector is crucial to its effectiveness as a gene therapy vehicle. A vector for use in gene therapy or research is preferably resistant to degradation by light, heat, contact with lab equipment or medical devices, and enzymes. Identification of factors that confer protection to viral vectors would greatly advance the field of genetic research, more so if viral vectors stably expressing protective factors were developed. To identify viral vectors with improved stability, the linear DNA molecules encode a factor which potentially confers improved stability to an virus. The factor can be from any origin or synthetically made. The library of viral vectors is exposed to destabilizing conditions. Destabilizing conditions include, for instance, exposure to degradative enzymes or chemicals, heat, cold, and mechanical disruption. Any surviving viral vectors are then identified by, for example, transducing a second population of host cells, maintaining the transduced cells, and observing plaque formation or virus growth. A stock of virus with improved resistance to destabilizing conditions can be prepared by harvesting and purifying the surviving virus and, optionally, propagating the survivors in an appropriate cell line.

The utility of viral vectors in gene therapy methods and research protocols can be limited by immunogenicity of the vector in vivo. Many indications and research methods require multiple administration of a viral vector to achieve a desired effect. With repeated administration of a virus in vivo, an immune response is generated by the body against the virus. Ultimately, the immune response will likely interfere with the ability of a viral vector to deliver nucleic acid molecules to host cells. Therefore, it would be advantageous to construct a viral vector able to avoid, for example, antibodies or other blood-borne proteins, such as complement proteins, which neutralize virus. In this aspect, the linear DNA molecule encodes a putative coat protein that is not recognized or prevents recognition by antibodies or other blood-borne proteins that are directed to wild-type virus. The putative coat protein can, itself, allow the virus to not be recognized by neutralizing proteins, e.g., antigenic epitopes are abrogated. Alternatively, the putative coat protein can bind to proteins in the blood stream that do not neutralize the virus, but mask binding sites for neutralizing antibodies and the like. Selecting the viral vector comprising the desired feature comprises exposing the library of viral vectors to neutralizing antibodies and/or other blood-borne proteins and identifying the viral vector that does not bind the neutralizing antibodies and/or other blood-borne proteins or is not neutralized. For example, virus-specific antibodies are immobilized in an affinity column. The library of viral vectors is passed through the column whereupon most vectors will bind to the attached antibodies. Viral vectors that completely pass through the affinity column are vectors that are not recognized by neutralizing antibodies. Of course, multiple rounds of screening and amplification may be required. Alternatively, the library of viral vectors is incubated in a blood sample comprising neutralizing antibodies or proteins or administered to an animal which produces neutralizing antibodies. Viral vectors that are not bound by the neutralizing antibodies or other blood-borne proteins can be isolated and used, for example, for multiple administrations in vivo. Antibodies and other neutralizing proteins that bind wild-type viral vectors can be generated and purified using methods well known in the art. The linear DNA molecules comprising a DNA fragment encoding a putative coat protein can be synthesized or isolated from any source. The linear DNA molecules can encode, for example, proteins that are inserted into various regions of the adenoviral coat, e.g., a fiber protein, hexon protein, penton base protein, pIIIa, or pIX. The putative coat protein can be a chimeric coat protein.

Viral growth and replication is a potent selection strategy. Viral vectors with high titers are extremely useful in genetic research and therapy. High titers of virus are often required for gene therapy procedures. A major concern of physicians and researchers is the ability to obtain sufficient amounts of viral vectors to administer to a patient to achieve a therapeutic effect. It would, therefore, be advantageous to construct a viral vector able to reproduce rapidly using the method of the present invention. To this end, the linear DNA molecule encodes a viral peptide potentially involved in viral replication. The viral peptide desirably confers to the virus the ability to replicate quickly, preferably more quickly than a wild-type virus, in order to achieve a great number of progeny virus. In terms of the present inventive method, cells are transduced with the library of viral vectors. The first population of host cells or a second population of host cells can be used to propagate the viral vector library. Selecting the viral vector comprising the desired feature comprises identifying the adenoviral vector that produces the most progeny. Preferably, the cells are transduced with virus at a relatively low multiplicity of infection. After a suitable period of time, e.g., about 24 hours, the viral vectors are harvested and purified from the transduced cells. The best replicating vectors will comprise a majority of the population of isolated virus. The isolated pool of viral vectors is then transduced into another population of cells, allowed to propagate, and surviving virus is harvested. Repeating the process will skew the viral population for the most efficiently replicating viral vectors. Once a pool of viral vectors is selected, titration curves are performed to identify the viral vector or viral vectors that produce high titers of virus. Of course, one of ordinary skill in the art will appreciate that the method described above is merely exemplary and that numerous other methods are available to determine rate of viral reproduction and virus titer. The above-described selection strategy effectively identifies viruses that can grow and reproduce with minimal intervention by the investigator.

In addition to screening viral peptides, viral libraries, in particular adenoviral libraries, created as described herein also are especially suited for identifying and isolating eukaryotic peptides. Adenovirus is used as a viral vector because it is easy to use, can be produced in high titers (i.e., up to about $10^{13}$ viral particles/ml), transfers genes efficiently to nonreplicating, as well as replicating cells (see, for example, review by Crystal, *Science*, 270, 404–410 (1995)), and exhibits a broad range of host- and cell-type specificity. Adenoviral vectors can be manipulated to accept large DNA molecules up to about 36 kb. In addition, adenoviral vectors can be constructed so that infection of a host cell does not kill or seriously interfere with host cell functioning. Thus, the function of a eukaryotic peptide or functional nucleic acid sequence can be determined in the context of its natural intracellular or cell surface environment in vitro or in vivo. It will be appreciated that determining the function of eukaryotic peptides in eukaryotic cells is more accurate than other methods wherein peptides are screened in bacterial cells or in soluble form in vitro.

The linear DNA molecules can encode any cellular peptide or functional nucleic acid sequence. Of course, the action of the putative peptide or functional nucleic acid sequence must be detectable in the cell or the animal, either directly or indirectly. Preferably, the linear DNA molecules are isolated from a number of different organisms. Library construction and methods of using a viral library rely on the creation of a diverse population of gene elements. The probability of identifying a novel peptide or a peptide with improved activity over a wild-type peptide is dependent on the diversity of the pool of linear DNA molecules. It is, therefore, advantageous to look to several potential sources for a desired feature. It is also advantageous to mutate the linear DNA molecules potentially comprising the desired feature to further diversify the population of genetic elements.

In one embodiment, the linear DNA molecules of the library of viral vectors encode a putative cell differentiation peptide. Examples of known differentiation factors include fibroblast growth factor and myogenic regulatory factors, which induce development of the cells of muscle cell lineage. The linear DNA molecules can encode a known cell differentiation factor that has been mutated. Alternatively, the linear DNA molecules can comprise random pieces of DNA isolated from a host cell genome, the genome of a closely related organism, or the genome of an all-together unrelated organism. To select the viral vector comprising the desired feature, the present inventive method further comprises transducing a second population of host cells that are not terminally differentiated with the library of viral vectors. Preferably the cells are maintained free from any interaction with differentiation factors in the environment. Transduced differentiated cells comprise a viral vector comprising a functional cell differentiation peptide. Identifying the transduced differentiated cells can be accomplished by, for example, detecting peptides associated with a particular differentiated cell type, observing changes in cell morphology, and the like.

The method of the present invention also can be used to identify transcription trans-activators or repressors or promoter trans-activating or repressing factors. As is understood in the art, some promoters are responsive to factors in the intracellular environment. For instance, promoters associated with transcription of adenoviral late genes are dependent on expression of genes located in the early regions of the adenoviral genome. A number of promoters are similarly responsive to factors to induce gene transcription. Using the methods described herein, novel promoter trans-activating factors can be identified. In this embodiment, the linear DNA molecule encodes at least one putative promoter trans-activating factor. Selecting the adenoviral vector with a desired feature comprises transducing cells comprising a quiescent promoter operably linked to a nucleic acid encoding a detectable gene product with the library of viral vectors, wherein the quiescent promoter can be transactivated. Cells used in the present inventive method can be any kind of eukaryotic cell, so long as the cells can be infected by the particular virus used. When the putative promoter trans-activating factor is functional, the quiescent promoter will be activated, thereby inducing expression of the detectable gene product. Transduced cells comprising the viral vector comprising a desired feature are identified by detecting the detectable gene product. Similarly, the present inventive method can be employed to identify a promoter repressor. In this embodiment, the transduced cells comprise an active promoter operably linked to a nucleic acid sequence encoding a detectable gene product. The active promoter must be able to be repressed. Selecting the viral vector comprising the desired feature comprises detecting reduced expression of the detectable gene product subsequent to infection with the viral vector library. Of course, any detectable gene product is appropriate for use in this embodiment of the present invention. The detectable gene product can be a marker protein, such as, for example, green fluorescent protein or luciferase. The detectable gene product can also comprise a protein or peptide that confers resistance to an antibiotic. A promoter trans-activating factor or repressor can be generated and selected to modulate only one specific promoter. Of course, such a system of trans-activation or repression would find utility in in vivo gene therapy wherein expression of a therapeutic product must be carefully controlled.

In another preferred embodiment of the present invention, the linear DNA molecules encode a putative inhibitor of a toxic protein. Toxins are routinely taken up by a cell from the extracellular environment and are frequently formed, for example, from the build-up of metabolic byproducts within the cell. To combat the constant borage of harmful substances, most cells have evolved protective factors that neutralize, digest, or remove toxins. Identification of these protective factors or production of novel protective factors could revolutionize the treatment of some metabolic disorders. The detrimental effects of toxic proteins to a host cell are an inherent difficulty of studying inhibition of toxic proteins in vivo and in vitro. Therefore, when using a library of viral vectors to identify a putative inhibitor of a toxic protein, the library of viral vectors is transduced into a second population of host cells comprising a nucleic acid sequence encoding a toxic protein desirably under the control of an inducible promoter. As such, the toxic protein will not be expressed and potentially harm the cell until induced by the investigator. Selecting the viral vector comprising a desirable feature comprises inducing the inducible promoter to express the toxic protein and identifying the cells that survive expression of the toxic protein. The protective factor or the linear DNA molecule encoding the protective factor then can be determined. Placing expression of a toxic protein under the control of an inducible promoter alleviates the problems associated with toxin research. The toxic protein is expressed intracellularly and, therefore, is not handled by technicians in its harmful form. The toxic protein is expressed after infection by the library of viral vectors so as not to interfere with the infection process. The strategy described herein provides a reasonable method to attribute any protective effect to the putative protective protein.

Cell death is not always induced by toxins or metabolic waste. Cells naturally undergo a cascade of events leading to cell death, named apoptosis or programmed cell death. Apoptosis is part of normal cell physiology, although uncontrolled apoptosis has been linked to human degenerative diseases. Identification of factors that inhibit programmed cell death would give physicians and researchers another therapeutic option in treating such degenerative disorders. Conversely, several therapeutic agents administered to patients to treat disease act by inducing apoptosis in diseased cells. A major drawback of such therapies is the bystander or collateral killing of normal, non-diseased cells. While one option to minimize apoptosis induction in non-diseased cells is to target the therapeutic agent to diseased cells, another attractive strategy is to render non-diseased cells resistant to the therapy.

To identify an anti-apoptotic agent, a library of viral vectors, preferably constructed as described herein, comprises linear DNA molecules encoding a putative anti-apoptotic agent. The library of viral vectors is transduced into a second population of host cells that are capable of undergoing induced apoptosis. The viral vector comprising a desired feature, an anti-apoptotic agent, is selected by inducing apoptosis in the transduced cells and identifying the transduced cells in which apoptosis is inhibited. To induce apoptosis, cells are contacted with a molecule or ligand that triggers signal transduction cascades that ultimately lead to programmed cell death, which includes a reduction in cell volume, nuclear condensation, cell blebbing, and endonucleolytic degradation of DNA at nucleosomal intervals. Apoptotic proteins or polypeptides available to induce apoptosis in a cell include Fas, FasL, FADD, MORT-1, Caspase-8 (FLICE), Caspase-10, IκB, ΔIκB, TNF-α, TNF-β, an adenoviral E1A product, an adenoviral E4 protein (e.g., E4/ORF4), and the like. Cells comprising a viral vector encoding a functional anti-apoptotic agent are easily recognized in that all cells not comprising an anti-apoptotic factor will die. If desired, the surviving cells can be maintained and the viral vectors isolated and purified. The anti-apoptotic agent can be identified. The linear DNA molecules encoding the functional anti-apoptotic agent also can be identified, and used to stably transduce other cells, thereby creating a population of apoptosis-resistant cells.

In addition to inhibitors of cell death caused by toxins or apoptosis, factors that protect host cells from pathogen-induced cell death also can be identified using viral libraries, such as those constructed as described herein. By "pathogen" is meant any microbe or parasite that disrupts cell functioning such that death occurs. It is known that infection by some viruses actually protects host cells from pathogens. Therefore, it is plausible that factors encoded by a viral genome have a protective effect in a host cell or animal. In addition, cells have evolved protective proteins to combat pathogens. In either case, identification of protective proteins or generation of novel proteins that protect cells from pathogen-induced cell death would have widespread utility in both clinical and research settings. In the clinic, the harmful effects of bacterial or fungal infections can be controlled. In the laboratory, cell loss due to contamination of cell lines could be minimized upon introduction of protective proteins into the cell culture. To identify a protective peptide, linear DNA molecules encoding putative peptides capable of protecting a cell against pathogen-induced cell death are inserted into recipient DNA molecules to form a library of viral vectors. The library of adenoviral vectors is transduced into a second population of host cells, which are subsequently contacted with a pathogen. Selecting a viral vector with a desired feature comprises identifying the cells in which cell death is inhibited. Any surviving cells can be maintained, and, if desired, the linear DNA molecule that encodes the protective peptide, or the protect peptide itself, can be isolated.

In that the present inventive method can involve administration of a library of viral vectors to an animal, the present invention has particular utility in screening putative therapeutic factors. By "therapeutic factor" is meant a peptide or functional nucleic acid sequence that alleviates or inhibits, in whole or in part, a disease or ailment. As used herein, a therapeutic factor can affect, for example, the nervous system, genitourinary ailments, cancer, infectious disease, and cardiovascular abnormalities, as well as miscellaneous other health nuisances. Therapeutic factors identified by the present inventive method can be used to treat, for example, sleep disorders, ALS (Lou Gehrig's Disease), Alzheimer's Disease, epilepsy, multiple sclerosis, Parkinson's Disease, peripheral neuropathies, Schizophrenia, depression, anxiety, spinal cord injury, traumatic brain injury, or acute, chronic, or inflammatory pain. Therapeutic factors can be identified to treat genitourinary ailments, which include, for example, benign prostatic hyperplasia (BPH), impotence, neurogenic bladder, urinary incontinence, kidney failure, and end stage renal disease. Therapeutic factors useful in treating cancer such as, for example, cancer of the bladder, brain, breast, colorectal, esophageal, head & neck, liver/hepatoma, lung, melanoma, ovarian, pancreatic, prostate, stomach, testicular, uterine/endometrial, leukemias, and lymphomas, also can be identified using the present inventive method. Therapeutic factors can be identified to treat infectious diseases that include, but are not limited to, chlamydia, herpes, malaria, human papilloma virus (HPV), AIDS/HIV, pneumococcal pneumonia, influenza, meningitis, hepatitis, and tuberculosis. Therapeutic factors for treating cardiovascular diseases such as, for example, neovascular diseases, ischemia, congestive heart failure, coronary artery disease, arrhythmia, atherosclerosis, increased LDL/HDL ratios, restenosis after angioplasty or in-stent restenosis, stroke, sickle cell anemia, and hemophilia, can be identified, as well as therapeutic factors associated with the alleviation of, for example, obesity, organ transplantation/transplant rejection, osteoporosis, alopecia, arthritis, allergies (such as to ragweed, pollen, and animal dander), cystic fibrosis, diabetes, macular degeneration, glaucoma, and hearing loss. One of ordinary skill in the art will appreciate that animal models exist for many of the disease states identified above. A library encoding a putative therapeutic factor for a given disease is administered to an animal model for that disease. For additional information regarding animal models of disease, see, for example, *Immunodeficient Mice in Oncology* (Contributions to Oncology, Vol. 42), Fiebig & Berger (Editors), S. Karger Publishing (July 1992); *Man and Mouse: Animals in Medical Research,* William D. M. Paton, ASIN: 0192861468; *Genetic Models of Immune and Inflammatory Diseases* (Serono Symposia Usa), Abbas &. Flavell, Eds., USA Serono Symposia, ASIN: 0387946497; *Urinary System (Monographs on Pathology of Laboratory Animals),* $2^{nd}$ Ed., Jones et al. (Editors), Springer Verlag (June 1998), ISBN: 0944398766; *What's Wrong with My Mouse?: Behavioral Phenotyping of Transgenic and Knockout Mice,* Jacqueline N. Crawley, John Wiley & Sons (Mar. 10, 2000), ISBN: 0471316393; *The Scid Mouse: Characterization and Potential Uses* (Current Topics in Microbiology and Immunology, Vol. 152), R. W. Compans (Editor), Springer Verlag (May 1990), ISBN: 0387515127; *Strategies in Transgenic Animal Science,* Monastersky & Robi (Editors), Amer. Society for Microbiology (July 1995), ISBN: 1555810969; *Pathology of Tumours in Laboratory Animals: Tumours of the Mouse,* $2^{nd}$ Ed., Turusov & Mohr (Editors), Iarc Scientific Publications, Vol. 002, No. 111, Oxford Univ. Press (February 1994), ISBN: 9283221117; *Laboratory Animals in Vaccine Production and Control: Replacement, Reduction, and Refinement* (Developments in Hematology and Immunology), Hendriksen & Nijhoff (October 1988), ISBN: 0898383986; *Motor Activity and Movement Disorders: Research Issues and Applications* (Contemporary Neuroscience), Sanberg et al. (Editors), Humana Pr. (January 1996), ISBN: 0896033279; *Cardiovascular and Musculoskeletal Systems* (Monographs on Pathology of Laboratory Animals), Jones et al. (Editors), Springer Verlag (September 1991), ISBN: 0387538763; *CRC Handbook of Animal Models for the Rheumatic Diseases,* Greenwald & Diamond (Editors), CRC Press (November 1988), ISBN: 0849329884; *Experimental and Genetic Rat Models of Chronic Renal Failure,* Gretz & Strauch, S. Karger Publishing (February 1993), ISBN: 3805554990; *Central Nervous System Diseases: Innovative Animal Models from Lab to Clinic* (Contemporary Neuroscience), Emerich et al. (Editors), Humana Pr. (November 1999), ISBN: 089603724X; *Experimental Models of Diabetes,* John H. McNeill (Editor), CRC Press (January 1999), ISBN: 0849316677; *Laboratory Animals: An Introduction for Experimenters,* $2^{nd}$ Ed., A. A. Tuffery (Editor), John Wiley & Son Ltd. (Jun. 27, 1995), ISBN: 0471952575; *Animal Models in Cardiovascular Research* (Developments in Cardiovascular Medicine, Vol. 153), David R. Gross, Kluwer Academic Publishers (June 1994), ISBN: 0792327128; *Anxiety, Depression, and Mania* (Animal Models of Psychiatric Disorders, Vol. 3), Soubrie (Editor), S. Karger Publishing (December 1990), ISBN: 3805552475; *Toxicity Assessment Alternatives: Methods, Issues, Opportunities,* Salem & Katz (Editors), Humana Pr (July 1999), ISBN: 0896037878; and *Pathobiology of the Aging Mouse: Nervous System, Special Senses (Eye and Ear), Digestive System, Integumentary System and Mammary Gland, and Musculos,* Mohr et al. (Editors), Int'l Life Sciences Inst., Vol. 2 (October 1996), ISBN: 0944398464.

With respect to therapeutic factors, the viral vector comprising the desired feature is selected by observing a change in the disease state of the animal. For example, when the desired therapeutic factor is an angiogenic peptide, the viral vector comprising the desired feature is selected by detecting neovascularization in the animal. Neovascularization can be detected using animal models known in the art, such as the mouse ear model, the rat hindlimb ischemia model, and the impaired pig heart model. Conversely, if the therapeutic factor is an anti-angiogenic factor, the viral vector comprising the desired feature is selected by detecting a reduction in neovascularization in the animal. If desired, multiple rounds of screening can be performed to identify a one or more viral vectors encoding the most effective therapeutic factors or to identify two or more therapeutic factors that affect the desired biological response.

In addition to screening for therapeutic factors, introduction of a multiplicity of genetic elements into an animal provides a novel method of immune system activation. Viral vectors are particularly appropriate for introducing potentially antigenic determinants to the immune system and have previously been used as antigen-presenting vectors. The members of the library of viral vectors also can be engineered to dramatically increase infection of immune effector cells. Adenoviral vectors are especially suited for this embodiment in that unlike other expression vectors, adenoviral vectors are not integrated into the host cell genome. This aspect of adenovirus is advantageous in inducing an immune response in that long-term expression of antigens can be harmful to an animal. To induce an immune response, the linear DNA molecule encodes at least one putative antigen. Administration of the library of viral vectors, desirably a library of adenoviral vectors, induces an immune response in the animal to the potential antigens. Preferably, at least one putative antigen is a tumor cell antigen, a viral antigen, or a bacterial antigen. Alternatively, at least one putative antigen is derived from a virus, a prokaryotic or eukaryotic pathogenic organism, a multicellular parasite, or the like. A viral library encoding a multiplicity of putative antigens provides a method to present to the animal many antigenic determinants from a given pathogen. The putative antigen can be expressed intracellularly and/or be present on the coat protein of the adenovirus. Antigens produced intracellularly are presented to the immune system via the major histocompatibility complex (MHC) I. Antigens taken up by cells from the environment are presented to the immune system via MHC II. By displaying antigens via both MHC I and MHC II cell surface structures, a highly efficient immune response involving both the humoral and cell-mediated arms of the immune system is induced. In contrast, currently employed methods of inducing an immune response to, for example, tumor cells, elicit only one arm of the immune system. For further discussion of immune responses, see, for example, Abbas et al., *Cellular and Molecular Immunology,* $3^{rd}$ Ed., W.B. Saunders Co., Philadelphia, Pa. (1997). Other advantages of using a library of viral vectors to induce an immune response are that specific antigenic determinants need not be known, whole and infective pathogens are not introduced to the animal, and potentially antigenic peptides that are usually masked by immune-avoidance processes of the pathogen can be exposed to an animal's immune system. Use of the method of the present invention to induce an immune response to a wide array of antigens finds utility in vaccine research and antibody production. Subsequent to infection with a library of viral vectors, sera from the infected animal can be sampled and antibodies specific to a plurality of antigens harvested.

Alternatively, as discussed above, a library of viral vectors can be introduced into an animal, preferably a human, to select for viral vectors comprising desirable characteristics for use in therapeutic modalities. Novel vectors that, for example, remain in the body for prolonged periods of time, do not elicit an immune response, or are targeted to a specific cell type, are of great commercial and therapeutic value. Such vectors are better able to infect cells in vivo than wild-type virus. In other words, delivery of the viral vectors comprising the desirable feature to target cells is enhanced. Viral vectors comprising such advantageous characteristics cannot be efficiently selected for under in vitro conditions. In vitro conditions cannot, for instance, mimic the actions of the liver or the immune system in removing or neutralizing virus from the body.

In order to identify viral vectors with at least one desired feature, a library of viral vectors comprising linear DNA molecules encoding a potentially desirable feature is constructed and administered to an animal. The animal is maintained for a period of time, after which a sample is collected from the animal in order to recover at least one viral vector from the sample. The sample can be taken from whole blood, sera, cells, tissue, or any organ of the body. The animal is maintained for a period of time to ensure that a change in phenotype is achieved. When the potentially desirable feature is a peptide, the period of time wherein the animal is maintained before a sample is removed depends on the particular assay or promoter used to drive transcription of the peptide. Preferably, the animal is maintained for about five minutes to about 30 days, although the animal can be maintained for as few as one or two minutes or, on the other hand, longer than 30 days.

Selecting for a desired feature in vivo is particularly useful to identify viral vectors with desirable properties for gene therapy. For example, oftentimes delivery of genetic material to a patient should be targeted to a specific region of the body, e.g., adenovirus preferentially infects one cell type or cells expressing a particular receptor over other cells. Unwanted side effects can occur if a therapeutic protein is expressed in normal cells in addition to diseased cells. Targeting of an expression vector to a particular cell type, e.g., tumor cells, or organ also minimizes the amount of total virus needed to be administered to achieve a therapeutic effect. In another aspect, the vector is not targeted to specific cells, per se, but instead more efficiently recognizes or infects a desired cell type. Therefore, to identify a targeting moiety, the present inventive method comprises constructing a library of viral vectors encoding, for example, putative ligands for host cellular receptors, administering the library of viral vectors to an animal, maintaining the animal for a period of time, collecting a sample of cells from the animal, recovering viral vectors from transduced cells in the sample, and identifying at least one virus that is specifically targeted to the cells of the sample. Alternatively, a sample of cells is collected from the animal, transduced cells are recovered from the sample, and at least one linear DNA molecule is identified that allows viral targeting to the cells of the sample. For example, a pool of adenoviral vectors are removed and purified from a tumor. The purified vectors are propagated, and readministered to an animal. Preferably, the adenoviral vectors of the library are ablated for receptor binding to non-targeted cell types, i.e., the virus no longer binds integrins or to CAR to avoid entry into non-targeted cells that express this molecule. Vectors are again removed and purified from a tumor. Further selection processes are performed to isolate an adenoviral vector that selectively targets a cell type of choice. With repeated rounds of screening, a viral vector can be constructed that distinguishes a diseased cell from a healthy cell. The present invention contemplates optional repeated rounds of selection to identify a linear DNA molecule encoding a desirable feature.

A library of viral vectors administered to an animal also can be used to identify viral vectors with increased persistence in vivo. Avoidance of clearance mechanisms of the body and increased circulation time allows a vector more time to reach target cells. For example, adenoviral vectors are typically cleared from circulation within minutes and are cleared from the body within about 7–10 days. It is not completely understood why a majority of adenoviral vectors are cleared quickly while very low levels of adenoviral vectors can be recovered from the blood stream several hours post-administration. Those vectors that remain in vivo for several minutes, preferably several hours or more, i.e., 1, 3, 5, or 7 days, post-administration and remain able to transduce cells or propagate are said to have a prolonged half-life in vivo or an extended circulation time. Linear DNA molecules encoding peptides potentially associated with increased persistence or half-life of a virus in vivo are provided. Peptides potentially associated with persistence or with increased ability of a vector to reach target tissues can include peptides involved in immune system avoidance, avoidance of neutralizing antibodies and other blood-borne proteins, avoidance of scavenger cells, reticuloendothelium system avoidance, resistance to degradative enzymes, the ability to cross endothelial or epithelial barriers, and the like. A library of viral vectors comprising the linear DNA molecules is constructed and administered to an animal. After administering the library of viral vectors to the animal, the present inventive method further comprises maintaining the animal for a period of time, collecting a sample (e.g., blood) from the animal, and recovering at least one adenoviral vector. The viral vector recovered from the sample has a prolonged half-life in circulation. If using adenovirus, the animal is preferably maintained for five minutes or longer before adenovirus is recovered. One of ordinary skill in the art will understand that the longer the animal is maintained before vectors are recovered, the better adapted the recovered adenoviral vectors will be for remaining in vivo for prolonged periods of time.

With respect to in vivo embodiments of the present invention, a library of viral vectors desirably is administered to an animal in a pharmaceutical composition, which comprises the library of viral vectors and a pharmaceutically acceptable carrier. Any suitable pharmaceutically acceptable carrier can be used within the context of the present invention. Appropriate formulations include, for example, aqueous and non-aqueous solutions, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid carrier, for example, water, immediately prior to use. Extemporaneous solutions and suspensions can be prepared from sterile powders, granules, and tablets of the kind previously described. Preferably, the pharmaceutically acceptable carrier is a buffered saline solution. When a library of viral vectors is introduced into an animal to elicit an immune response, the pharmaceutical composition optionally further comprises an inflammatory agent and/or an adjuvant. Suitable compositions are further discussed in International Patent Application WO 00/34444.

The pharmaceutical composition described herein can be delivered via various routes and to various sites in an animal body (see, e.g., Rosenfeld et al., *Clin. Res.*, 39(2), 311A (1991)). One skilled in the art will recognize that although more than one route can be used for administration, a particular route can be more appropriate than another route, depending on the particular embodiment of the present inventive method. Local or systemic delivery can be accomplished by administration comprising application or instillation of the formulation into body cavities, inhalation or insufflation of an aerosol, or by parenteral introduction, comprising intramuscular, intravenous, peritoneal, subcutaneous, intraarterial, intraocular, and intradermal administration, as well as topical administration. Of course, the routes of administration discussed herein are merely exemplary. The present inventive methods are not dependent on the particular route of administration or dose of virus administered.

Those of ordinary skill in the art can easily make a determination of the proper dosage of the library of viral vectors. A variety of factors will impact the dosage that is administered, although the proper dosage is such that the desired effect, e.g., an immune or therapeutic response, is realized. Specifically, the dosage will vary depending upon the particular method of administration. Preferably, about $1 \times 10^4$ to about $1 \times 10^{15}$ virus particles are administered to an animal, although more or less virus can be administered. Most preferably, about $1 \times 10^8$ to about $1 \times 10^{12}$ virus particles are administered to an animal. Wherein a library of viral vectors is administered to an animal in order to select for a virus with desired characteristics, the amount of virus administered should be sufficient to ensure efficient infection of, for example, target cells, and subsequent recovery of vectors.

In addition, the time and cost to develop pharmaceutical products will be reduced by the techniques described herein. Any data generated from such techniques, including data concerning the identification of gene products or functional nucleic acid sequences, the activity of gene products or functional nucleic acid sequences, the interaction of gene products or functional nucleic acid sequences, and the like, can be compiled, organized, screened, assayed, analyzed and/or sorted in any various manner, including those manners known to the ordinarily skilled bioinformatics artisan, in order to determine, for example, pathological pathways. For instance, the data generated using any of the techniques described herein can be compiled into a database, e.g., a database accessible via the internet or other distributed network, to query, provide access, present, and analyze the gathered information in a meaningful format. Such a database provides a request entry system for certain techniques described herein, and may include terms for such request, including financial terms, field(s) of use, any granted rights, deliverables, timing, and ownership of results and discoveries.

EXAMPLES

The following examples further illustrate the present invention but, of course, should not be construed as in any way limiting its scope.

Example 1

This example illustrates a preferred method of generating a library of adenoviral vectors. A cosmid containing adenovirus type 5 (Ad5) genome with an expression cassette replacing the E1 region was created. The expression cassette comprised an RSV promoter and thymidine kinase polyadenylation signal that directed transcription toward the adenoviral left inverted terminal repeat (ITR). Into the expression cassette a cDNA library was cloned, the source of which was adenovirus serotype-5 (Ad5) RNA isolated from infected HeLa cells.

Twenty 10 cm plates containing HeLa cells at 50% confluency were infected with wild-type Ad5 at a multiplicity of infection (m.o.i.) of 10. Approximately 4 mg of total RNA was isolated using Promega's RNeasy kit following the manufacturer's instructions (Promega, Madison, Wis.)). Approximately 4 µg of polyA mRNA was isolated from 2 mg of total RNA using Qiagen's OligoTex kit (Qiagen, Valencia, Calif.). mRNA was converted to cDNA utilizing the Stratagene ZAP Express cDNA library kit following the manufacturer's instructions with minor modifications (Stratagene, La Jolla, Calif.). The cDNA fragments were flanked with SpeI and SwaI sites at the 5' terminus and 3' terminus, respectively.

The cDNA (100 ng) was ligated with 1 µg of lambda UNIZAP-XR vector (Stratagene), packaged into phage heads in vitro using Giga Pack Gold extract (Stratagene), and introduced into XL-1 Blue cells. The library comprised approximately $2.5 \times 10^5$ plaque forming units (pfu).

An innoculum obtained from a culture of non-transduced XL-1 Blue grown overnight was started in luria broth (LB) comprising 0.2% maltose and 10 mM $MgSO_4$. The resulting stock of XL-1 Blue was transduced with the packaged phage and plaqued in top agar (NZY broth+0.6% agar) at approximately $5 \times 10^4$ plaques/150 mm agarose plate for 5–6 hours following standard protocols. Phage was isolated from the cell culture by overnight incubation in 10 ml of cold saline media (SM) buffer per plate. The titer of the eluted phage was $4.5 \times 10^9$ pfu/ml.

Approximately 20 µg of phage DNA was isolated from 50,000 plaques utilizing a Promega Wizard Lambda Prep kit. The phage DNA was digested with SwaI and SpeI and purified using Qiagen's plasmid purification cartridge. The purified DNA comprising the cDNA fragments (100 ng) was ligated to 1 µg of XbaI- and SwaI-restricted pACE(RTXS)E3(10X) previously treated with shrimp alkaline phosphatase. pACE(RTXS)E3(10X), illustrated in FIG. 1, is a recipient DNA molecule comprising an adenoviral genome and a phage packaging site. The ligation reaction was packaged into phage capsids in vitro using Giga Pack Gold extract (Stratagene). XL-1 Blue cells were transduced with the packaged DNA and plated on 150 mm agarose plates for overnight incubation. Colonies were harvested from the plates using luria broth (LB) and were brought to 30% glycerol before being snap frozen and stored at −80° C. Approximately 1 ml of the cosmid library was incubated overnight at 30° C. in media comprising kanamycin to select for the adenoviral vector genome comprising cDNA inserts. Cosmid library DNA (200 µg) was isolated and purified using a Qiagen endotoxin-free DNA column. The cosmid library had a total complexity of approximately $4 \times 10^5$ colony forming units.

The cosmid library was converted to an adenoviral library on 293 cells. Cosmid library DNA isolated as described above was restricted with PacI and extracted with phenol and 25:25:1 phenol/$CHCL_3$/isoamyl alcohol. The DNA was then precipitated with ethanol, dried, and resuspended in pyrogen-free water. To infect cells that support the production of adenovirus, 5 µg of purified DNA was added to water mixed with $CaCl_2$ to a final volume of 250 µl, 100 mM $CaCl_2$. Approximately 250 µl of 2X Hanks Balanced Saline (HBS) was quickly added to the DNA, mixed, and incubated at room temperature for 1–2 minutes. The entire DNA mixture was added to a 60 mm plate comprising $1 \times 10^6$ 293 cells, previously fed with media containing 5% fetal bovine serum. The cells were allowed to incubate in the presence of the DNA for approximately four hours, after which the cells were washed with 1 ml of 1 mM EGTA in HBS, and then washed twice again with media comprising 2% serum.

Approximately 5 ml of media comprising 5% serum was added to the plates, which were then allowed to incubate.

Five days later, the transduced cells were freeze-thawed three times. One ml of lysate was added to 10 cm plates comprising 293 cells at 70% confluency. One hour later, 5 ml of media comprising 5% serum was added to each plate. At four days after transduction, cytopathic effect (CPE) was observed, and the cells were freeze-thawed three times to create a cell lysate comprising a library of adenoviral vectors. Analysis of the lysate revealed an adenoviral vector titer of $4\times10^7$ pfu/ml of lysate.

This example demonstrates that a library of adenoviral vectors can be generated using the method of the present invention.

Example 2

This example illustrates the use of a library of adenoviral vectors to successfully isolate a cDNA encoding the Ad5 E1 13S transcript.

A549 cells grown to 70% confluence on 60 mm plates were infected with 1 ml of lysate comprising a library of adenoviral vectors prepared as described in Example 1. A549 cells are human lung carcinoma cells that support full viral infection and lytic growth. A549 cells do not, however, provide E1 complementing activity, which is required for propagation of the viral genome used to construct the library of adenoviral vectors. The cells were maintained for 5 days before undergoing three freeze-thaw cycles to release a first passage (P1) lysate comprising a library of adenoviral vectors. Two additional passages were carried out to create second passage (P2) and third passage (P3) lysates. The adenoviral vectors that survive the three passages must comprise a cDNA fragment encoding a peptide with E1 complementing activity. By the third passage, full viral infection was observed at two days post-infection, whereupon the infected cells were frozen. With the initiation of selection, the relative abundance of adenoviral vectors fell 10-fold from that of the first passage, specifically from $4\times10^7$ to $3.8\times10^6$ pfu/ml.

DNA sequences with E1 complementing activity were identified. Lysates from P1 and P3 were used to PCR amplify all sequences present within the expression cassette. The primers used in the PCR reaction, annealed to the Ad5 genome and RSV promoter, ensure specificity of the reaction to the viral library. The two primers annealed 744 bp apart in the vector. The PCR reaction was performed, and the products were separated on an agarose gel. A single prominent band of 1.8 kb was generated from the P3 lysate, while no bands were observed from the P1 lysate. The cDNA insert was predicted to be approximately 1 kb in size. These data are consistent with the selection and expansion of adenovirus observed both phenotypically and by pfu analysis. The PCR material was subjected to Southern blot analysis employing a probe specific for the E1 region. The results identified the major band to have homology with the viral E1 region and to have a size predicted for the E1A 13S splice variant. Direct sequencing of the PCR product confirmed the insert to be derived from the E1A 13S transcript.

This example demonstrated the utility of the present inventive method in identifying a linear DNA encoding a desirable feature by selecting for a desired function. The selection methods described herein can be modified to suit any particular embodiment of the present inventive method.

Example 3

This example demonstrates a method of screening a library of adenoviral vectors to select for an adenoviral vector encoding a putative angiogenic factor. The method described in this example also can be employed to screen a multi-gene adenoviral vector library for an adenoviral vector encoding factors which enhance or repress angiogenesis.

A library of adenoviral vectors is constructed as described herein. The members of the library of adenoviral vectors comprise linear DNA molecules comprising DNA fragments encoding putative angiogenic factors. The desired dosage of adenoviral vectors is delivered to the ears of anesthetized nude mice and anesthetized C57BL/6 mice (12 mg/kg xylazine and 60 mg/kg ketamine, IP delivery) by subcutaneous injection at the base of the ear. At various days post-injection, the animals are observed for gross changes to the treated area and perfusion levels are measured by scanning laser Doppler perfusion imaging. The ears can be harvested, perfusion fixed with Zinc/Tris fixative, embedded in paraffin, and sectioned in 5 µm layers and stained for CD31 antigen using immuno-staining. Changes in blood vessel numbers are quantitated and vessel quality assessed using methods known in the art. Adenoviral vectors that promote the desired degree of angiogenesis can be identified by isolating vectors or vector DNA from the ear tissue of the infected mouse.

Example 4

This example demonstrates a method of screening a library of adenoviral vectors for enhanced targeting and persistence in vivo.

The recipient DNA molecule of Example 1 is employed to create a library of adenoviral vectors genomes. Linear DNA molecules comprising DNA fragments encoding putative targeting moieties are inserted into the adenoviral genome such that fusion proteins are generated consisting of the putative targeting moiety and the adenoviral fiber, hexon, penton base, or pIX proteins. The source of the linear DNA molecules can be pools of random DNA molecules artificially synthesized or can be taken from a pool of preselected linear DNA molecules. The library of adenoviral vector genomes is converted to a library of adenoviral vectors. The adenoviral vectors are preferably ablated for receptor binding to the CAR and/or integrins, etc., to avoid entry of the virus into non-target cells expressing those molecules.

A purified library of adenoviral vectors is injected into an animal and adenoviral vectors comprising a desired feature are selected and amplified. Methods of screening the library of adenoviral vectors depend on the desired feature. To select for adenoviral vectors having a prolonged half-life, the animal is maintained for a period of time, after which a sample of blood is taken. Cells and platelets are spun down, allowing recovery of the adenoviral vectors. The recovered adenoviral vectors are amplified on permissive cell lines, such as 293-HA cells, which permit replication and amplification of CAR and integrin-ablated vectors, and additional rounds of screening are performed.

If the desired feature is the ability of the adenovirus to target a receptor-bearing tumor, the library of adenoviral vectors is injected into a nude mouse bearing a tumor, such as, for example, an AE25 tumor. AE25 tumors can complement E1-deleted adenoviral vectors. The ability of the tumor cells to complement E1-deleted vectors allows propagation of the desired vectors within the tumor tissue and facilitates isolation of the desired vectors. Adenoviral vectors are then isolated from the tumor, amplified, and purified. Additional rounds of selection can be performed if desired.

If desired, an adenoviral vector can be selected that targets and infects a cell despite the presence of neutralizing antibodies. Such an adenoviral vector is most desired in gene therapy protocols. To select for such a vector, the mouse bearing the tumor described above is passively immunized with anti-adenovirus antibodies. Adenoviral vectors isolated using this procedure are both targeted to a particular cell type and have prolonged half-life.

All of the references cited herein, including patents, patent applications, and publications, are hereby incorporated in their entireties by reference.

While this invention has been described with an emphasis upon preferred embodiments, it will be obvious to those of ordinary skill in the art that variations of the preferred embodiments may be used and that it is intended that the invention may be practiced otherwise than as specifically described herein. Accordingly, this invention includes all modifications encompassed within the spirit and scope of the invention as defined by the following claims.

What is claimed is:

1. A library of adenoviral vectors, wherein each member of the library comprises (i) a first heterologous DNA encoding a vascular endothelial growth factor (VEGF), wherein the first heterologous DNA is common to each member of the library of adenoviral vectors, and (ii) a second heterologous DNA encoding a second gene product, wherein the second heterologous DNA varies between the members of the library of adenoviral vectors.

2. The library of claim 1, wherein the first heterologous DNA and/or the second heterologous DNA is operably linked to an inducible promoter.

3. The library of claim 1, wherein the first heterologous DNA and the second heterologous DNA are under the control of separate regulatory elements.

4. The library of claim 1, wherein the first heterologous DNA and the second heterologous DNA are under the control of a bi-directional promoter.

5. The library of claim 1, wherein the second gene product is fused to an activation domain, and the first gene product is fused to a DNA binding domain.

6. A library of serotype 35 adenoviral vectors, wherein each member of the library comprises (i) a first heterologous DNA encoding a vascular endothelial growth factor (VEGF), wherein the first heterologous DNA is common to each member of the library of adenoviral vectors, and (ii) a second heterologous DNA encoding a second gene product, wherein the second heterologous DNA varies between the members of the library of adenoviral vectors.

* * * * *